United States Patent
Akita et al.

(10) Patent No.: US 10,132,225 B2
(45) Date of Patent: Nov. 20, 2018

(54) FUEL CONSUMPTION CALCULATION UNIT, FUEL CONSUMPTION MEASURING APPARATUS, AND EXHAUST GAS MEASURING APPARATUS

(71) Applicant: HORIBA, Ltd., Kyoto (JP)

(72) Inventors: Masanobu Akita, Kyoto (JP); Hiroshi Nakamura, Kyoto (JP); Ichiro Asano, Kyoto (JP); Masayuki Adachi, Kyoto (JP)

(73) Assignee: Horiba, Ltd., Kyoto (JP)

( * ) Notice: Subject to any disclaimer, the term of this patent is extended or adjusted under 35 U.S.C. 154(b) by 458 days.

(21) Appl. No.: 14/456,668

(22) Filed: Aug. 11, 2014

(65) Prior Publication Data
US 2015/0046101 A1  Feb. 12, 2015

(30) Foreign Application Priority Data

Aug. 12, 2013  (JP) .................. 2013-167426
Nov. 28, 2013  (JP) .................. 2013-246491

(51) Int. Cl.
*F01N 13/00* (2010.01)
*G01N 33/22* (2006.01)
(Continued)

(52) U.S. Cl.
CPC .......... *F01N 13/008* (2013.01); *F02B 77/086* (2013.01); *F02D 41/1445* (2013.01);
(Continued)

(58) Field of Classification Search
CPC .. F01N 13/008; F02B 77/086; F02D 41/1441; F02D 41/1438; F02D 41/1445;
(Continued)

(56) References Cited

U.S. PATENT DOCUMENTS 3,844,920 A    10/1974 Burgett et al.
4,372,155 A *   2/1983 Butler .................. F02B 77/086
                                                          73/114.72
(Continued)

FOREIGN PATENT DOCUMENTS

CN    001287614 A    3/2001
CN       1490507 A    4/2004
(Continued)

OTHER PUBLICATIONS

Akita et al. SAE Int. J. Commer. Veh. Apr. 8, 2013, vol. 6, Issue 1, p. 183-189, "In-Situ Real-Time Fuel Consumption Measurement Using Raw Exhaust Flow Meter and Zirconia AFR Sensor."
(Continued)

*Primary Examiner* — Leslie J Evanisko
*Assistant Examiner* — Leo T Hinze
(74) *Attorney, Agent, or Firm* — Brooks Kushman P.C.

(57) ABSTRACT

The present invention is intended to, at the time of directly measuring a flow rate of exhaust gas flowing through an exhaust gas flow path and an air-fuel ratio of the exhaust gas, and on the basis of the flow rate and air-fuel ratio of the exhaust gas, calculating fuel consumption, reduce a measurement error of the fuel consumption. Also, the invention is a fuel consumption calculation unit that, with use of an exhaust gas flow rate obtained by a flow rate sensor provided in an exhaust gas flow path through which exhaust gas of an engine flows, and an air-fuel ratio obtained by an air-fuel ratio sensor provided in the exhaust gas flow path, calculates fuel consumption of the engine, and on the basis of the air-fuel ratio obtained by the air-fuel ratio sensor, changes a value of exhaust gas density used for the calculation of the fuel consumption.

10 Claims, 12 Drawing Sheets

(51) Int. Cl.
*G01F 1/00* (2006.01)
*G01M 15/10* (2006.01)
*G01N 9/00* (2006.01)
*G01N 33/00* (2006.01)
*F02B 77/08* (2006.01)
*F02D 41/14* (2006.01)
*G01F 9/00* (2006.01)
*G01F 1/66* (2006.01)

(52) U.S. Cl.
CPC .................. *G01F 1/00* (2013.01); *G01F 1/66* (2013.01); *G01F 9/001* (2013.01); *G01M 15/104* (2013.01); *G01N 9/00* (2013.01); *G01N 33/0062* (2013.01); *G01N 33/22* (2013.01); *F02D 41/1456* (2013.01); *F02D 2200/0614* (2013.01); *F02D 2200/0625* (2013.01); *G01N 2033/0068* (2013.01)

(58) Field of Classification Search
CPC ...... F02D 2200/0625; G01F 1/66; G01F 9/00; G01M 15/102; G01M 15/10
See application file for complete search history.

(56) References Cited

U.S. PATENT DOCUMENTS

| | | | |
|---|---|---|---|
| 5,574,211 A * | 11/1996 | Shimada | G01D 5/2417 73/1.38 |
| 6,382,014 B1 * | 5/2002 | Breton | F01N 13/008 73/114.76 |
| 6,470,732 B1 * | 10/2002 | Breton | F01N 13/008 73/114.69 |
| 6,553,818 B1 | 4/2003 | Blumke et al. | |
| 6,701,963 B1 | 3/2004 | Hill | |
| 9,453,751 B2 * | 9/2016 | Akita | G01F 9/00 |
| 2001/0010031 A1 | 7/2001 | Takamoto et al. | |
| 2008/0209886 A1 | 9/2008 | Zillmer et al. | |
| 2015/0046101 A1 | 2/2015 | Akita et al. | |

FOREIGN PATENT DOCUMENTS

| | | |
|---|---|---|
| CN | 101008588 A | 8/2007 |
| CN | 101196435 A | 6/2008 |
| CN | 101975663 A | 2/2011 |
| CN | 102155962 A | 8/2011 |
| CN | 102346105 A | 2/2012 |
| CN | 102472694 A | 5/2012 |
| DE | 102006047526 A1 | 4/2008 |
| EP | 2 687 829 A1 | 1/2014 |
| JP | 63-181924 U1 | 11/1988 |
| JP | 02234021 | 9/1990 |
| JP | 11-230797 A | 8/1999 |
| JP | 2001-208584 A | 8/2001 |
| JP | 2001-215213 A | 8/2001 |
| JP | 2001-338670 A | 12/2001 |
| JP | 2002-227711 A | 8/2002 |
| JP | 2005-002830 A | 1/2005 |
| JP | 2005-155619 A | 6/2005 |
| JP | 2009-250935 A | 10/2009 |
| JP | 2010-223702 A | 10/2010 |
| JP | 2011-185097 A | 9/2011 |
| JP | 2012-127858 A | 7/2012 |
| WO | 99-35480 A1 | 7/1999 |
| WO | 2011108586 A1 | 9/2011 |
| WO | 2012/124062 A1 | 9/2012 |

OTHER PUBLICATIONS

Akita et al. Society of Automotive Engineers of Japan (JSAE) Annual Congress May 22, 2013, 6 Pages, "Real-time Fuel Consumption Measurement Using Raw Exhaust Flow Meter and Zirconia AFR Sensor."

Akita et al. SAE World Congress Apr. 16-18, 2013, 11 Pages, "In-Situ Real-Time Fuel Consumption Measurement Using Raw Exhaust Flow Meter and Zirconia AFR Sensor."

Horiba Ltd, Pacifico Yokohama Exhibition Hall, May 22-24, 2013, 13 Pages, "Automotive Engineering Exposition."

Dthce Action dated May 25, 2017 issued for Japanese patent application No. 2013-246491, 2 pgs.

EESR dated Sep. 25, 2014 issued for European patent application No. 14 001 743.5, 5 pgs.

Office Action dated Jan. 15, 2016 issued for U.S. Appl. No. 14/282,816, 8 pgs.

Office Action dated Mar. 23, 2017 issued for Japanese patent application No. 2013-167302, 2 pgs.

Decision to grant a patent dated May 23, 2017 issued for Japanese patent application No. 2013-167302, 5 pgs.

Office Action dated Mar. 23, 2017, issued for Japanese Patent Application No. 2013-167426, 4 pgs.

Office Action dated Feb. 1, 2018 issued in Chinese Patent Application No. 201410201105.3.

Official Communication pursuant to Article 94(3) EPC dated Apr. 4, 2018 issued for European Patent Application No. 14 001 743.5. 6 pgs.

Office Action dated May 2, 2018 issued for Chinese Patent Application No. 201410394518.8, 13 pgs.

* cited by examiner (1) CONVENTIONAL METHOD (2) PRESENT EMBODIMENT

| AIR-FUEL RATIO | $O_2$ CONCENTRATION | $H_2O$ CONCENTRATION | COMBUSTIBLE COMPONENTS | | | OTHER COMPONENTS | |
|---|---|---|---|---|---|---|---|
| | | | CO CONCENTRATION | HC CONCENTRATION | $H_2$ CONCENTRATION | $N_2$ CONCENTRATION | $CO_2$ CONCENTRATION |
| ⋮ | ⋮ | ⋮ | ⋮ | ⋮ | ⋮ | ⋮ | ⋮ |
| 10 | 0.5 | 11 | 10.5 | 0.2 | 5 | 65.9 | 6.9 |
| 11 | 0.6 | 11.8 | 8.7 | 0.1 | 4 | 66.8 | 8 |
| ⋮ | ⋮ | ⋮ | ⋮ | ⋮ | ⋮ | ⋮ | ⋮ |
| 16 | 1.9 | 11 | 0.7 | 0.1 | 1 | 73.3 | 12 |
| 17 | 3.2 | 10.6 | 0.6 | 0.1 | 0.9 | 73.6 | 11 |
| ⋮ | ⋮ | ⋮ | ⋮ | ⋮ | ⋮ | ⋮ | ⋮ |

VALUES ARE REPRESENTED IN UNIT OF VOL%

FIG.9

FUEL CONSUMPTION CALCULATION UNIT, FUEL CONSUMPTION MEASURING APPARATUS, AND EXHAUST GAS MEASURING APPARATUS

CROSS-REFERENCE TO RELATED APPLICATIONS

This application claims priority to JP Application No. 2013-167426, filed Aug. 12, 2013, and JP Application No. 2013-246491, filed Nov. 28, 2013, the disclosures of which are incorporated in their entirety by reference herein.

TECHNICAL FIELD

The present invention relates to a fuel consumption measuring apparatus that measures fuel consumption of an engine, and in particular, to a fuel consumption calculation unit and fuel consumption calculation program that calculate the fuel consumption. Also, the present invention relates to an exhaust gas measuring apparatus that measures the concentration of each of components contained in exhaust gas of an engine, or the like, and in particular, to an apparatus that is preferably used at the time of measuring fuel consumption of the engine on the basis of the concentration of the component.

BACKGROUND ART

The improvement of fuel efficiency is one of important challenges in research and development of a vehicle, and for further improvement, it is important to measure instantaneous fuel consumption related to behavior of an engine.

To instantaneously measure fuel consumption, direct measurement by a fuel flowmeter is commonly used. However, in the case of a completed vehicle, the measurement using a fuel flowmeter is difficult. Also, it is not easy to, without disturbing any fuel system condition, place a fuel flowmeter in a fuel flow path.

For this reason, for example, a method (carbon balance method) that obtains emission mass from respective exhaust gas component concentrations in exhaust gas diluted by a CVS, and from the emission mass, calculates fuel consumption is used (e.g., JPA-2-234021). The carbon balance method is one that calculates fuel consumption from amounts of carbon contained in respective components of $CO_2$, CO, and HC in exhaust gas.

However, in the case of the method that introduces the diluted exhaust gas diluted by the CVS into an exhaust gas analyzer through a sampling flow path, and measures the component concentrations of $CO_2$, CO, and HC in the exhaust gas, it takes time for the diluted exhaust gas to be introduced into the exhaust gas analyzer through the sampling flow path, and therefore a response delay occurs. For example, measurement of fuel consumption of a vehicle that frequently performs a fuel cut and switching to electrical driving makes a response delay due to gas congestion caused by the sampling flow path particularly noticeable, and therefore may be unsuitable for the instantaneous fuel consumption measurement.

SUMMARY OF INVENTION

Technical Problem

The present inventor has been considering to instantaneously measure fuel consumption by directly measuring a flow rate of an exhaust gas flowing through an exhaust gas flow path and an air-fuel ratio of the exhaust gas, and from the flow rate and air-fuel ratio of the exhaust gas, calculating the fuel consumption. To calculate the fuel consumption, in addition to the flow rate and air-fuel ratio of the exhaust gas, exhaust gas density is used.

Meanwhile, as the exhaust gas density used for the calculation of the fuel consumption, a constant value determined by the type of fuel may be used. This is because it is considered that in the case where the air-fuel ratio is included in a lean region, the exhaust gas density hardly changes, and therefore an influence of the use of the constant value is practically ignorable. Also, another reason is because in measurement of fuel consumption of an engine or a vehicle, in particular, at the time of stationary operation, most of air-fuel ratios are usually included in the lean region.

However, in the case where the air-fuel ratio is included in a rich region, the exhaust gas density changes along with a change in the air-fuel ratio, and in measurement of fuel consumption of an engine or a vehicle, an air-fuel ratio may be included in the rich region depending on a load condition. In such a case, the use of the constant value for the exhaust gas density as described above causes a measurement error in fuel consumption.

Therefore, the present invention is mainly intended to, at the time of directly measuring a flow rate of exhaust gas flowing through an exhaust gas flow path and an air-fuel ratio of the exhaust gas, and on the basis of the flow rate and air-fuel ratio of the exhaust gas, calculating fuel consumption, reduce a measurement error of the fuel consumption.

Solution to Problem

That is, a fuel consumption calculation unit according to the present invention is one that, with use of an exhaust gas flow rate obtained by a flow rate sensor provided in an exhaust gas flow path through which exhaust gas of an engine flows, and an air-fuel ratio obtained by an air-fuel ratio sensor provided in the exhaust gas flow path, calculates fuel consumption of the engine, and on a basis of the air-fuel ratio obtained by the air-fuel ratio sensor, changes exhaust gas density used for the calculation of the fuel consumption.

Also, a fuel consumption calculation program according to the present invention is one that, with use of an exhaust gas flow rate obtained by a flow rate sensor provided in an exhaust gas flow path through which exhaust gas of an engine flows, and an air-fuel ratio obtained by an air-fuel ratio sensor provided in the exhaust gas flow path, calculates fuel consumption of the engine, and on a basis of the air-fuel ratio obtained by the air-fuel ratio sensor, changes exhaust gas density used for the calculation of the fuel consumption.

If so, the exhaust gas density used for the calculation of the fuel consumption is changed on the basis of the air-fuel ratio obtained by the air-fuel ratio sensor, and therefore a measurement error of the fuel consumption of the engine can be reduced. Also, the flow rate and air-fuel ratio of the exhaust gas flowing through the exhaust gas flow path are directly measured by the flow rate sensor and the air-fuel ratio sensor, and therefore a response delay occurring due to providing a conventional sampling flow path can be eliminated. For these reasons, the fuel consumption of the engine can be measured at high response speed and with high accuracy. Further, because of the direct measurement, a piping configuration can be simplified by eliminating the need for the conventional sampling flow path. Still further, a dilution device such as a CVS becomes unnecessary, and therefore the measuring apparatus can be downsized. In addition, for these reasons, apparatus cost can also be reduced.

In a region (lean region) where an air-fuel ratio is larger than a theoretical air-fuel ratio (stoichiometry), exhaust gas density is substantially constant on a fuel type basis, whereas in a region (rich region) where the air-fuel ratio is smaller than the theoretical air-fuel ratio, the exhaust gas density changes along with a change in air-fuel ratio. For this reason, desirably, in the case where the air-fuel ratio is included in the rich region, the fuel consumption calculation unit or the fuel consumption calculation program changes the exhaust gas density on the basis of the air-fuel ratio, and in the case where the air-fuel ratio is included in the lean region, uses a predetermined constant value as the exhaust gas density.

As a method for, in the case where the air-fuel ratio is included in the rich region, changing the exhaust gas density on the basis of the air-fuel ratio, (1) a method that, in a memory of the calculation unit, stores relational expression data indicating a relational expression between an air-fuel ratio and exhaust gas density in the rich region, and in the case where the air-fuel ratio obtained by the air-fuel ratio sensor is determined to be in the rich region, substitutes the air-fuel ratio into the relational expression to calculate the exhaust gas density corresponding to the air-fuel ratio, (2) a method that, in the memory of the calculation unit, stores table data indicating a table of each air-fuel ratio and exhaust gas density corresponding to the air-fuel ratio in the rich region, and in the case where the air-fuel ratio obtained by the air-fuel ratio sensor is determined to be in the rich region, derives exhaust gas density corresponding to the air-fuel ratio, or another method is possible.

Also, a fuel consumption measuring apparatus according to the present invention is one that measures fuel consumption of an engine, and provided with: a flow rate sensor that is provided in an exhaust gas flow path through which exhaust gas emitted from the engine flows and measures a flow rate of the exhaust gas flowing through the exhaust gas flow path; and a calculation unit that, with use of the exhaust gas flow rate obtained by the flow rate sensor, and an air-fuel ratio obtained by an air-fuel ratio sensor provided in the exhaust gas flow path, calculates the fuel consumption of the engine, wherein on a basis of the air-fuel ratio obtained by the air-fuel ratio sensor, the calculation unit changes exhaust gas density used for the calculation of the fuel consumption.

If so, the exhaust gas density used for the calculation of the fuel consumption is changed on the basis of the air-fuel ratio obtained by the air-fuel ratio sensor, and therefore a measurement error of the fuel consumption of the engine can be reduced. Also, the flow rate and air-fuel ratio of the exhaust gas flowing through the exhaust gas flow path are directly measured by the flow rate sensor and the air-fuel ratio sensor, and therefore a response delay occurring due to providing a conventional sampling flow path can be eliminated. For these reasons, the fuel consumption of the engine can be measured at high response speed and with high accuracy. Further, because of the direct measurement, a piping configuration can be simplified by eliminating the need for the conventional sampling flow path. Still further, a dilution device such as a CVS becomes unnecessary, and therefore the measuring apparatus can be downsized. In addition, for these reasons, apparatus cost can also be reduced.

For example, a zirconia type air-fuel ratio sensor is one that, in the case where combustion is included in the lean region, because $O_2$ remains in exhaust gas, calculates an air-fuel ratio on the basis of an increase in $O_2$ concentration with respect to the theoretical air-fuel ratio, and in the case where the combustion is included in the rich region, because combustible components (HC, CO, and $H_2$) are contained in the exhaust gas, calculates the air-fuel ratio on the basis of increases in concentrations of the combustible components with respect to the theoretical air-fuel ratio.

However, on occasions such as a cold start when an engine or the exhaust gas is not sufficiently warmed, $H_2O$ in the exhaust gas condenses in an exhaust pipe, and a large amount of $H_2O$ is lost in a path to a measuring point by the air-fuel ratio sensor. For this reason, as compared with exhaust gas immediately after emission from the engine, in the exhaust gas at the measuring point, concentrations of respective components are changed correspondingly to the lost $H_2O$ (specifically, the concentrations are higher than their true values).

Further, the air-fuel ratio sensor measures the air-fuel ratio on the basis of $O_2$ concentration or combustible component concentrations in the exhaust gas in which the large amount of $H_2O$ has been lost, and therefore an error is considered to occur in the measured air-fuel ratio as well.

For this reason, the present invention is mainly intended to accurately measure, in addition to an air-fuel ratio, various physical quantities related to exhaust gas, such as fuel consumption.

That is, the present invention relates to an exhaust gas measuring apparatus that utilizes a temperature sensor that measures temperature of exhaust gas emitted from an engine, and an air-fuel ratio sensor that is provided in an exhaust gas flow path through which the exhaust gas flows, and is characterized by being provided with the following constituent features:

(1) A related data storage part that stores a relationship between concentrations of respective components contained in the exhaust gas and an air-fuel ratio.

(2) A temporary concentration calculation part that refers to the related data storage part to calculate temporary H2O concentration that is H2O concentration corresponding to a measured air-fuel ratio obtained from the air-fuel ratio sensor.

(3) A lost H2O calculation part that, on the basis of saturated water vapor concentration at the exhaust gas temperature obtained from the temperature sensor, and the temporary H2O concentration, calculates a lost H2O amount that is an amount of H2O lost by condensation and the like in a path to a measuring point of the air-fuel ratio sensor after the emission from the engine.

If so, the lost H2O amount can be calculated, so that by taking into account the lost H2O amount, the exhaust gas immediately after the emission from the engine can be accurately analyzed, and for example, measurement accuracies of the air-fuel ratio and respective component concentrations, or measurement accuracies of fuel consumption and the like obtained from the air fuel ratio and the respective component concentrations can be improved.

In addition, as long as the temperature sensor is provided on an upstream side in the exhaust gas flow path with respect to the air-fuel ratio sensor, the effect of the present invention becomes noticeable; however, such a positional relationship may be reversed.

In order to improve the measurement accuracy of the air-fuel ratio, the present invention is preferably further provided with the following constituent feature (4):

(4) An air-fuel ratio amendment part that takes into account the lost H2O amount to amend the measured air-fuel ratio.

In order to improve the measurement accuracies of the component concentrations, the present invention is preferably further provided with the following constituent feature (5):

(5) A component concentration calculation part that refers to the related data storage part to thereby calculate the respective component concentrations corresponding to an amended air-fuel ratio that is the measured air-fuel ratio amended.

In order to improve the measurement accuracy of the fuel consumption, the present invention is preferably further provided with the following constituent features (6) and (7):

(6) A density calculation part that calculates exhaust gas density on the basis of the respective component concentrations calculated in the component concentration calculation part.

(7) A fuel consumption calculation part that calculates the fuel consumption of the engine on the basis of the exhaust gas density and the amended air-fuel ratio.

The component concentrations can be calculated through the amended air-fuel ratio as described in (4) and (5); however, the component concentrations can also be calculated through the following constituent feature (8):

(8) The temporary concentration calculation part refers to the related data storage part to thereby calculate the respective component concentrations corresponding to the measured air-fuel ratio obtained from the air-fuel ratio sensor, and the present invention is further provided with a component concentration calculation part that takes into account the lost H2O amount to amend one component concentration of the respective component concentrations calculated by the temporary concentration calculation part, and refers to the related data storage part to thereby calculate the other component concentrations corresponding to the amended one component concentration.

Advantageous Effects of Invention

According to the present invention configured as described, the exhaust gas density used for the calculation of the fuel consumption is changed on the basis of the air-fuel ratio obtained by the air-fuel ratio sensor, and therefore a measurement error of the fuel consumption can be reduced.

BRIEF DESCRIPTION OF THE DRAWINGS

FIG. 9 is a content diagram illustrating contents of a related data storage part in the present embodiment;

DESCRIPTION OF EMBODIMENTS

First Embodiment

In the following, a first embodiment of a fuel consumption measuring apparatus according to the present invention is described with reference to drawings.

Figure 1:
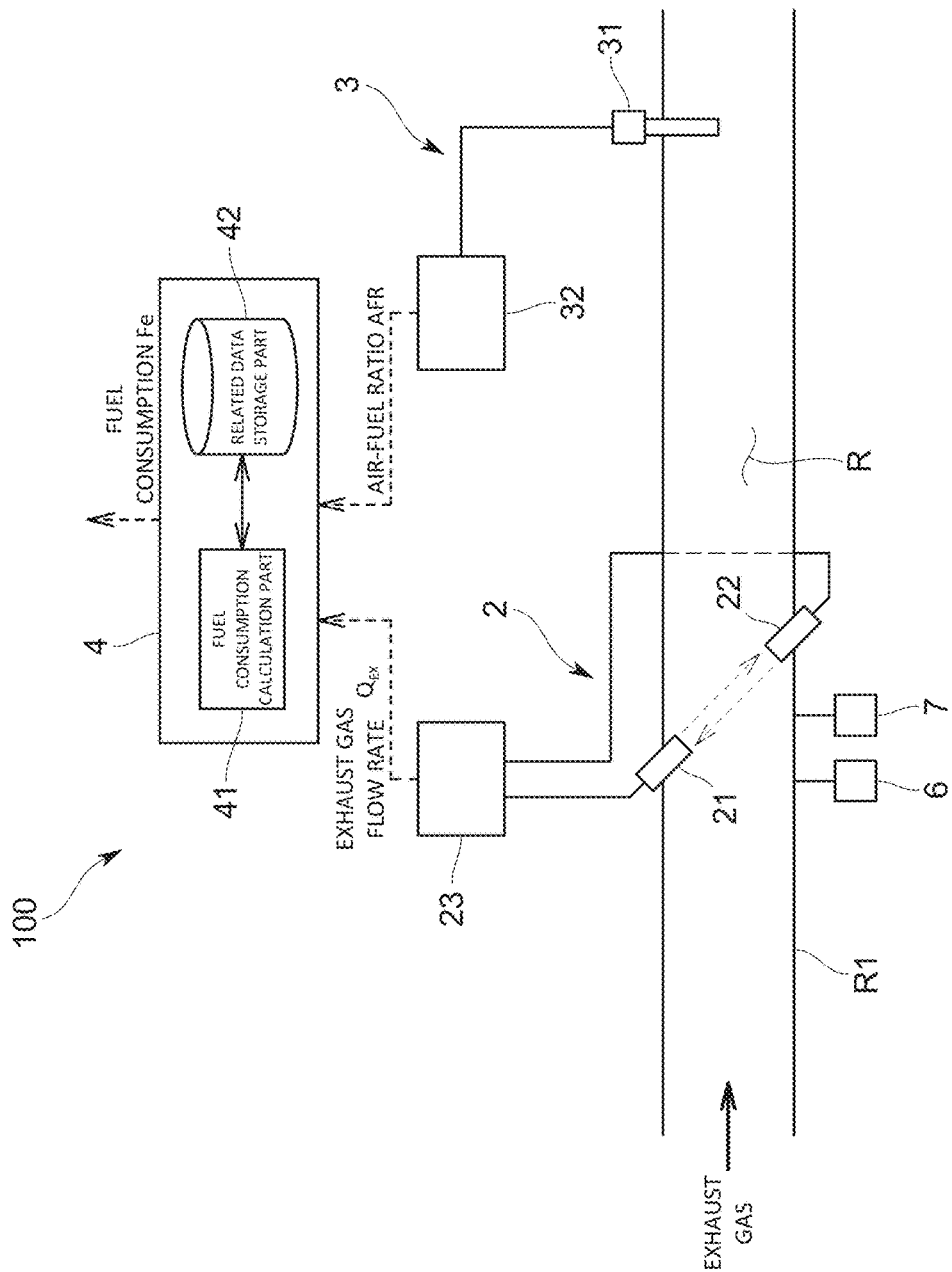
FIG. 1 is a diagram schematically illustrating a configuration of a fuel consumption measuring apparatus of the present embodiment.
Figure 2:
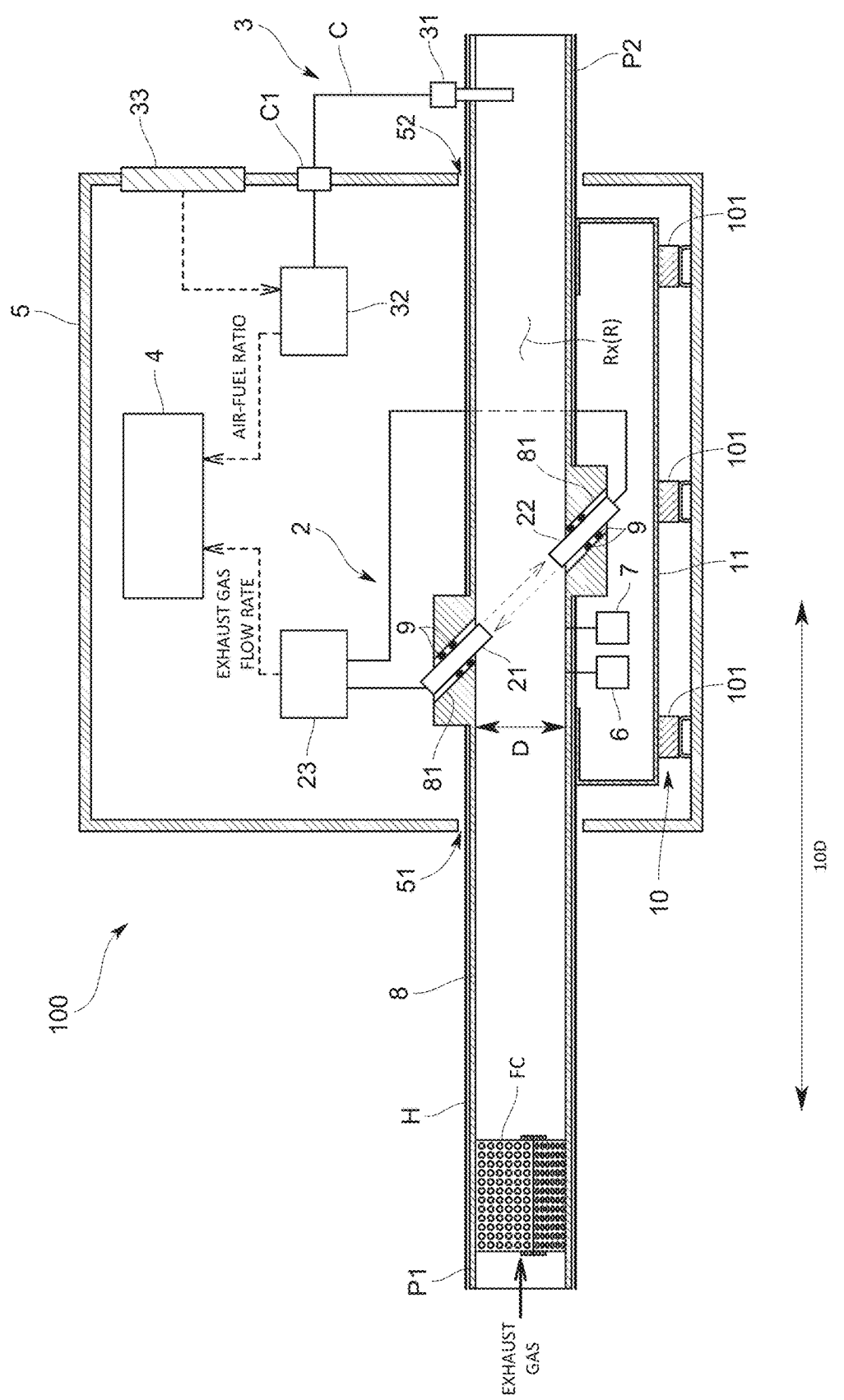
FIG. 2 is a schematic diagram illustrating a specific apparatus configuration in the same embodiment.

An exhaust gas measuring apparatus of the present embodiment is one that is used as a fuel consumption measuring apparatus 100 that measures fuel consumption (e.g., gas mileage or a fuel consumption rate) of an engine, and as illustrated in FIGS. 1 and 2, provided with: a sampling pipe 8 that is directly connected to a tail pipe (not illustrated) of an engine exhaust pipe; a flow rate sensor 2 that directly measures a flow rate QEX of exhaust gas flowing through the sampling pipe 8; an air-fuel ratio sensor 3 that is attached to the sampling pipe 8 on a downstream side with respect to the flow rate sensor 2; and a fuel consumption calculation unit 4 (hereinafter simply referred to as a calculation unit 4 as well) that, with use of the exhaust gas flow rate obtained by the flow rate sensor 2 and a measured air-fuel ratio obtained by the air-fuel ratio sensor 3, calculates the fuel consumption of the engine. The respective parts are described below.

Part Configuration 1: Sampling Pipe

The sampling pipe 8 is, for example, a straight pipe made of, for example, stainless steel, of which as illustrated in FIGS. 1 and 2, one end part P1 is directly connected to the tail pipe such that a total amount of the exhaust gas emitted from the engine is introduced, and constitutes an exhaust gas flow path referred to in claims. A side circumferential surface of the sampling pipe 8 is covered with a heater H, and thereby the sampling pipe 8 is configured to be able to prevent condensation of each component, especially water, contained in the exhaust gas to accurately perform after-mentioned various types of measurement.

Also, the sampling pipe 8 is made to penetrate through a separately provided housing 5, and inside the housing 5, the flow rate sensor 2, the fuel consumption calculation unit 4, and the like are contained. Between the sampling pipe 8 and the housing 5, an antivibration mechanism 10 is made to intervene, so that vibration of the sampling pipe 8, which is caused by vibration of the vehicle exhaust pipe, can be prevented from being directly transmitted the housing 5, and thereby an influence of the vibration on devices such as after-mentioned arithmetic processing devices (e.g., calculation parts 23 and 32, and the calculation unit 4) fitted in the housing 5 can be reduced. Specifically, the antivibration mechanism 10 is configured to include antivibration rubbers 101 provided between a lower surface of a supporting member 11 and a bottom surface of the housing 5.

Note that the sampling pipe 8 is configured to vibrate together with the exhaust pipe, and therefore in order to prevent the sampling pipe 8 from vibrating to come into contact with any of side wall opening parts 51 and 52 of the housing 5, opening diameters of the side wall opening parts 51 and 52 of the housing 5 are made larger than an outside diameter of the straight pipe member 8.

Part Configuration 2: Flow Rate Sensor

In the present embodiment, as the flow rate sensor 2, for example, a sensor of an ultrasonic type is used. The ultrasonic flow rate sensor 2 is one that is, as illustrated in FIGS. 1 and 2, provided with: first and second ultrasonic transceivers 21 and 22 that are paired and mutually oppositely arranged with being oblique to a flow path direction of the exhaust gas flow path R formed by the sampling pipe 8; and the calculation part 23 that outputs a transmission signal to one 21 (or 22) of the ultrasonic transceivers 21 and 22 as well as obtaining a reception signal from the other ultrasonic transceiver 22 (or 21), and thereby detects a propagation time of an ultrasonic pulse to calculate an exhaust gas flow velocity and the exhaust gas flow rate.

The paired ultrasonic transceivers 21 and 22 are fixed with being respectively inserted into insertion holes 81 provided in a side wall of the sampling pipe 8 inside the housing 5. The present embodiment is configured such that between outer circumferential surfaces of the ultrasonic transceivers 21 and 22 and inner circumferential surfaces of corresponding ones of the insertion holes 81, electrically insulating members 9 such as O-rings are made to intervene, respectively, which enables the ultrasonic transceivers 21 and 22 and the sampling pipe 8 to be insulated from each other to reduce electrical noise transmitted from the sampling pipe 8 to the ultrasonic transceivers 21 and 22. In addition, the antivibration rubbers 101 are also made to carry an electrical noise suppressing function. That is, the antivibration rubbers 101 fulfill an insulating function between the housing 5 and the sampling pipe 8, and therefore the electrical noise can be surely prevented from being transmitted from the housing 5 to the ultrasonic transceivers 21 and 22 through the sampling pipe 8.

Also, as described above, the sampling pipe 8 vibrates as a whole in response to the vibration of the vehicle exhaust pipe; however, by directly attaching the ultrasonic transceivers 21 and 22 to the sampling pipe 8, a change in relative positional relationship between them can be prevented to suppress a measurement error of the exhaust gas flow rate.

Physically speaking, the calculation part 23 is one that is provided with: an analog electric circuit including an amplifier and the like; a digital circuit including a CPU, memory, logic circuit, and the like; and an ADC, a DAC, and the like that serve as bridges between them, and in this embodiment, contained in the housing 5. Also, functionally, the calculation part 23 is one that performs operations equivalent to operations expressed by the following expressions (Expressions 1 and 2), and thereby calculates the flow rate of the exhaust gas. In addition, part or all of functions of the calculation part 23 may be transferred to the after-mentioned calculation unit 4.

$$v(t) = \frac{L}{2\cos\varphi}\left(\frac{1}{T_{dn}} - \frac{1}{T_{up}}\right) \quad \text{[Expression 1]}$$

Here, v(t) is the exhaust gas flow velocity [m/s], $T_{dn}$ a propagation time [s] of an ultrasonic wave in a downstream direction, $T_{up}$ a propagation tome of an ultrasonic wave in an upstream direction, L a distance [m] between the transceivers, and φ an angle [°] between the flow direction and an ultrasonic wave propagation axis.

The calculation part 23 uses the exhaust gas flow velocity v(t) obtained as described and a cross-sectional area of the exhaust gas flow path R to calculate a volumetric flow rate of the gas in a standard state according to the following expression.

$$q_{EX}(t) = k_{profile} \times A \times v(t) \times \frac{T_0}{T_{EX}(t)} \times \frac{p_{EX}(t)}{p_0} \quad \text{[Expression 2]}$$

Here, qEX(t) is an exhaust gas volumetric flow rate [m³/min] at time t in the standard state, kprofile an amendment factor based on a velocity distribution inside the exhaust gas circulation pipe R1, A the cross-sectional area [m²] of the exhaust gas circulation pipe R1, $T_0$ a standard temperature (=293.15) [K], TEX(t) exhaust gas temperature [K], pEX(t) exhaust gas pressure [kPa], and p0 a standard pressure (=101.3) [kPa].

In addition, the exhaust gas temperature TEX(t) and the exhaust gas pressure pEX(t) are respectively obtained by a temperature sensor 6 and a pressure sensor 7 attached near an upstream side of the ultrasound transceivers 21 and 22 in the sampling pipe 8 inside the housing 5.

Figure 3:
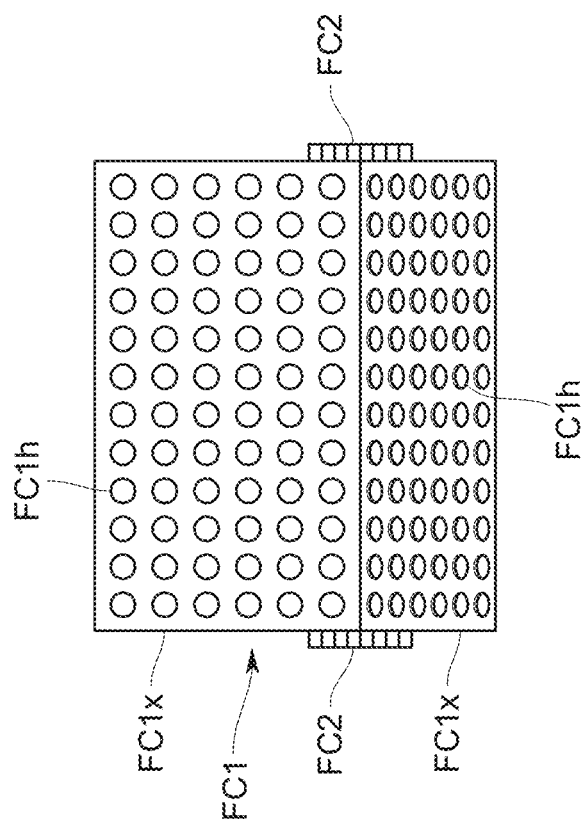
FIG. 3 includes front and side views illustrating a configuration of a flow conditioner in the same embodiment.
Figure 3:
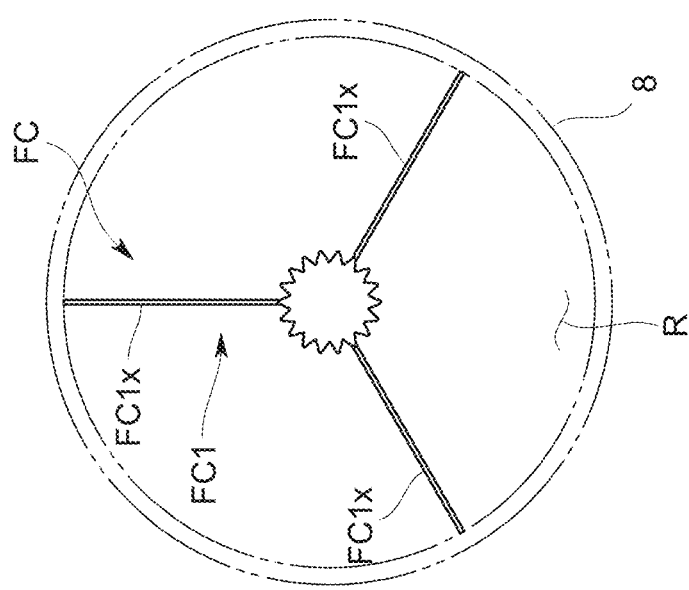

Meanwhile, in FIG. 2, a symbol FC provided on the upstream side of the ultrasonic flow rate sensor 2 represents a flow conditioner. The flow conditioner FC is one that is attached to the exhaust gas introduction port P1, which is a fore end port of the sampling pipe 8, or within a predetermined range near the exhaust gas introduction port P1, and for example, as illustrated in FIG. 3, provided with: a main body FC1 having a plurality of vanes FC1x that separate the exhaust gas flow path R into a plurality of sections along a circumferential direction; and end surface plates FC2 that are respectively provided on both end surfaces of the main body FC1.

The main body FC1 has the plurality of vanes FC1x at regular intervals in the circumferential direction. The main body FC1 in the present embodiment is configured by connecting one side parts of the plurality of vanes FCx. Also, each of the vanes FC1x is formed in a substantially rectangular shape, and formed with a plurality of through-holes FC1h.

The end surface plates FC2 are ones that are respectively provided on the both end surfaces (upstream and downstream side end surfaces) of the main body FC1 and formed in substantially circular shapes. Each of the end surface plates FC2 in the present embodiment is, along a circumferential direction in a circumferential edge part thereof, regularly formed with an uneven shape that is, for example, a triangular wave shape.

The flow conditioner FC can straighten a flow of the exhaust gas flowing into the ultrasonic flow rate sensor 2, and thereby eliminate disturbance in the flow velocity distribution of the exhaust gas flowing into the ultrasonic flow rate sensor 2, and therefore the exhaust gas flow rate can be more accurately measured.

Note that the ultrasonic flow rate sensor 2 is provided in a measuring flow path Rx and the air-fuel ratio sensor 3 is provided at an exhaust gas lead-out port P2, so that the ultrasonic flow rate sensor 2 and the air-fuel ratio sensor 3 are provided in the exhaust gas flow path R at a short distance equivalent to substantially the same position, and consequently provided within a range where a time lag in measurement between the ultrasonic flow rate sensor 2 and the air-fuel ratio sensor 3 does not occur and the composition of the exhaust gas does not change. That is, an air-fuel ratio sensor (not illustrated) is also provided near an exhaust gas outlet port of the engine of a vehicle, and a value of the sensor can also be used to calculate the fuel consumption; however, in this case, on a downstream side of the engine, a catalyst and the like are present to cause the accumulation of the exhaust gas, and therefore between a value of the exhaust gas flow rate obtained by the ultrasonic flow rate sensor 2 measuring the exhaust gas emitted from the tail pipe and an air-fuel ratio measured using the air-fuel ratio sensor inside the vehicle, a time lag occurs. For this reason, in the present embodiment, by providing the air-fuel ratio sensor 3 near the ultrasonic flow rate sensor 2, a measurement error due to the occurrence of the time lag can be eliminated to obtain accurate instantaneous fuel consumption. Further, in the present embodiment, it is preferable to provide the air-fuel ratio sensor 3 on a downstream side of the ultrasonic flow rate sensor 2, i.e., at the exhaust gas lead-out port P2. This is because, in the case of providing the air-fuel ratio sensor 3 on an upstream side of the ultrasonic flow rate sensor 2, i.e., at the exhaust gas introduction port P1, the air-fuel ratio sensor 3 serves as a resistor to give rise to disturbance in the flow velocity distribution of the exhaust gas, which becomes an error factor of a measured value of the ultrasonic flow rate sensor 2. By providing the air-fuel ratio sensor 3 on the downstream side of the ultrasonic flow rate sensor 2, without the occurrence of such unevenness in flow velocity, the exhaust gas flow rate can be accurately measured. Further, given that a flow path diameter of the exhaust gas flow path R is D, it is preferable to, on the upstream side of the ultrasonic flow rate sensor 2, provide a straight pipe having a distance (length) of 10D (ten times D) or more. This is because, in the case of providing a curved pipe in a position that is on the upstream side of and close to the ultrasonic flow rate sensor 2, unevenness occurs in the flow velocity distribution, which becomes an error factor of a measured value of the ultrasonic flow rate sensor 2.

Part Configuration 3: Air-Fuel Ratio Sensor

The air-fuel ratio sensor 3 is a zirconia type sensor that is, as illustrated in FIGS. 1 and 2, provided with: a direct insertion type sensing part 31 that is provided with being inserted on the downstream side of the ultrasonic flow rate sensor 2 in the exhaust gas flow path R; and the calculation part 32 that is electrically connected to the sensing part 31. The zirconia type air-fuel ratio sensor 3 can measure whether or not $O_2$ is excess or deficient as compared with combustion at a theoretical air-fuel ratio.

To specifically describe this, the sensing part 31 is one that has: a zirconia ($ZrO_2$) solid electrolytic body of which both surfaces are formed with electrodes; and an electric circuit (not illustrated) that detects electromotive force generated between the electrodes, or provides applied power between the electrodes, and in this embodiment, made to penetrate through the downstream side end part P2 of the sampling pipe 8 extending outside the housing 5. The electric circuit is one adapted such that in order to make the exhaust gas incorporated inside the air-fuel ratio sensor 3 equivalent to that at the theoretical air-fuel ratio, current flows through the zirconia solid electrolytic body so as to, in the case of combustion in the engine falls within a lean region, pump out excess $O_2$ in the incorporated exhaust gas, and in the case where the combustion falls within a rich region, pump in $O_2$ of which an amount corresponds to just combusting combustible components (CO, $H_2$, and HC) of the incorporated exhaust gas.

The calculation part 32 is one that is physically provided with: an analog electric circuit including an amplifier and the like; a digital circuit including a CPU, memory, logic circuit, and the like; and an ADC, a DAC, and the like that serve as bridges between them, and in this embodiment, contained in the housing 5. Also, functionally, the calculation part 32 is one that detects a value of the current, and calculates the air-fuel ratio from the excess or deficiency of $O_2$ concentration, which is obtained on the basis of the value, with respect to the theoretical air-fuel ratio. More specifically, in the lean region, the calculation part 32 calculates the air-fuel ratio on the basis of a predetermined theoretical expression from remaining $O_2$ concentration obtained from the value of the current, whereas in the rich region, the calculation part 32 obtains the air-fuel ratio by performing back calculation on the basis of an experimentally prepared calibration curve. The air-fuel ratio obtained by the air-fuel ratio sensor 3 is hereinafter referred to as a measured air-fuel ratio. In addition, part or all of functions of the calculation part 32 may be transferred to the after-mentioned calculation unit 4.

Meanwhile, in this embodiment, as illustrated in FIG. 2, a cable C extended from the sensing part 31 is connected to a connector C1 for connecting the sensing part 31 to the calculation part 32 contained in the housing 5. The connector C1 is provided through a side wall of the housing 5. As described, the air-fuel sensor 3 is provided outside the housing 5, and configured to be attachable/detachable through the connector C1, and thereby replacement work of the air-fuel sensor 3 can be facilitated. Also, on the side wall of the housing 5, an input part 33 for inputting setting parameters for the air-fuel sensor 3, such as an input panel, is provided. The setting parameters include a sensor constant set for each air-fuel sensor, and other parameters necessary for the air-fuel ratio measurement. By providing the input part 33 on the side wall of the housing 5 as described, the present embodiment is adapted to be able to, after installing or replacing the air-fuel ratio sensor 3, input the setting parameter for the air-fuel ratio sensor 3 on site. That is, the present embodiment is adapted to be able to do the replacement work of the air-fuel ratio sensor 3 and input work of the setting parameters for the air-fuel ratio sensor 3 in the same place, and thereby improves user-friendliness.

Part Configuration 4: Fuel Consumption Calculation Unit

The fuel consumption calculation unit 4 is one that is physically provided with: an analog electric circuit including an amplifier and the like; a digital circuit including a CPU, memory, logic circuit, and the like; and an ADC, a DAC, and the like that serve as bridges between them, and in this embodiment, contained in the housing 5.

Functionally, the fuel consumption calculation unit 4 fulfills functions as a fuel consumption calculation part 41, a related data storage part 42, and the like as illustrated in FIG. 1 by the CPU and its peripheral devices that cooperate according to a predetermined fuel consumption calculation program stored in the memory.

The fuel consumption calculation part 41 obtains exhaust gas flow rate data indicating the exhaust gas flow rate $Q_{EX}$ from the ultrasound flow rate sensor 2 as well as obtaining air-fuel ratio data indicating the air-fuel ratio AFR from the air-fuel ratio sensor 3. Further, the fuel consumption calculation part 41 uses the exhaust gas flow rate $Q_{EX}$ obtained by the ultrasonic flow rate sensor 2 and the air-fuel ratio AFR obtained by the air-fuel ratio sensor 3 to calculate the instantaneous fuel consumption Fe(t) according to the following expression.

$$Fe(t) = \frac{Q_{EX}(t)}{60} \times D_{EX} \times \frac{1}{AFR(t)+1} \quad \text{[Expression 3]}$$

Here, Fe(t) is a fuel consumption rate [g/s] at time t, $Q_{EX}(t)$ an exhaust gas flow rate [L/min] in the standard state (temperature: 293.15 K, pressure: 101.3 kPa) at time t, AFR(t) an air-fuel ratio at time t, and $D_{EX}$ exhaust gas density [kg/m$^3$].

In addition, the fuel consumption calculation part 41 displays the instantaneous fuel consumption Fe(t) calculated according to the above expression in a display part (not illustrated), or output the instantaneous fuel consumption Fe(t) to an upper level control device that controls the fuel consumption measuring apparatus 100. Besides, the calculation unit 4 may be one having an output part that, for example, prints the instantaneous fuel consumption Fe(t) obtained by the fuel consumption calculation part 41 on paper.

Figure 4:
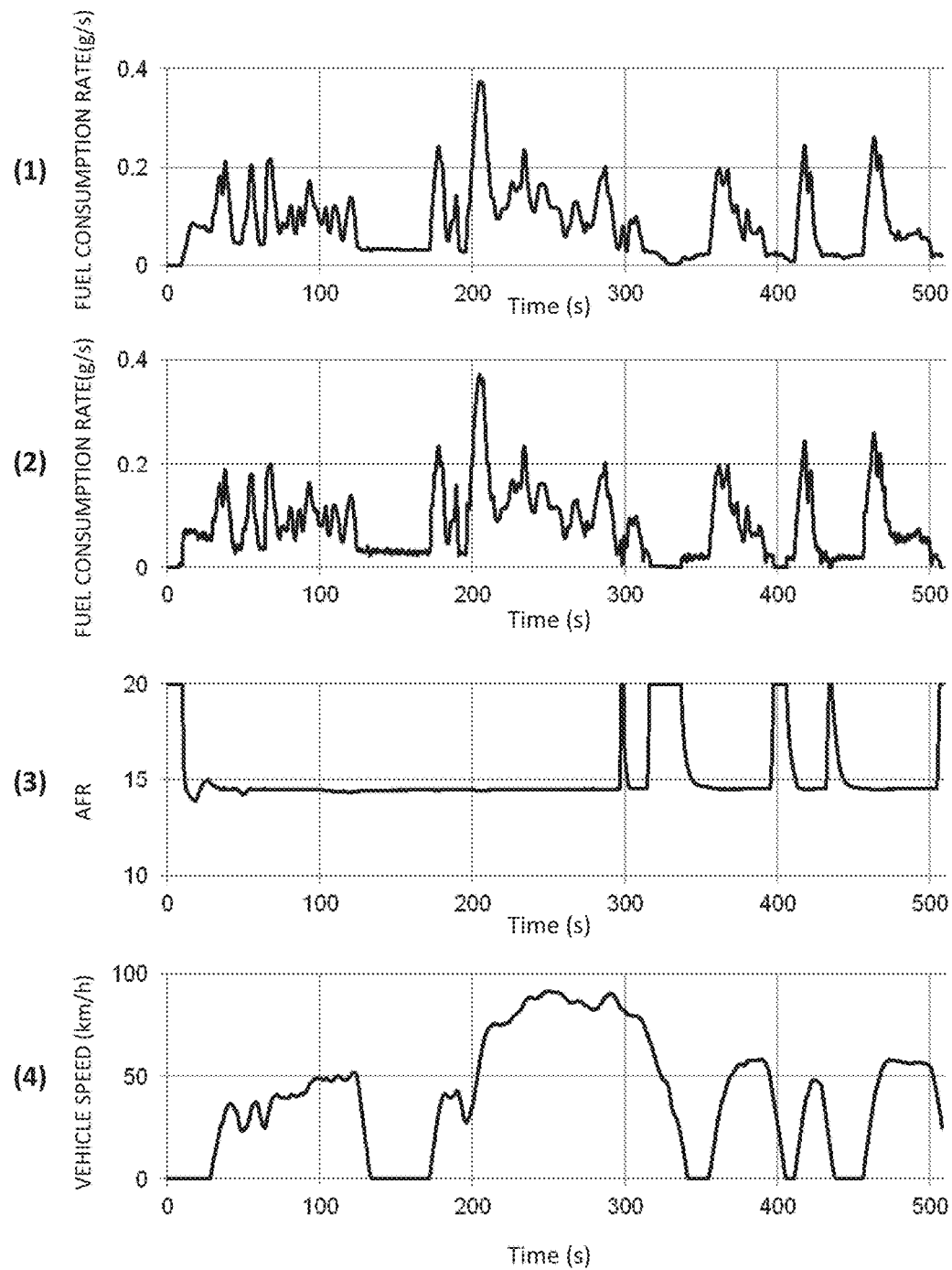
FIG. 4 is a diagram illustrating results of real-time measurement by the fuel consumption measuring apparatus of the present embodiment and real-time measurement by a dilute stream method, and the like (in the case of the cold start phase)
Figure 5:
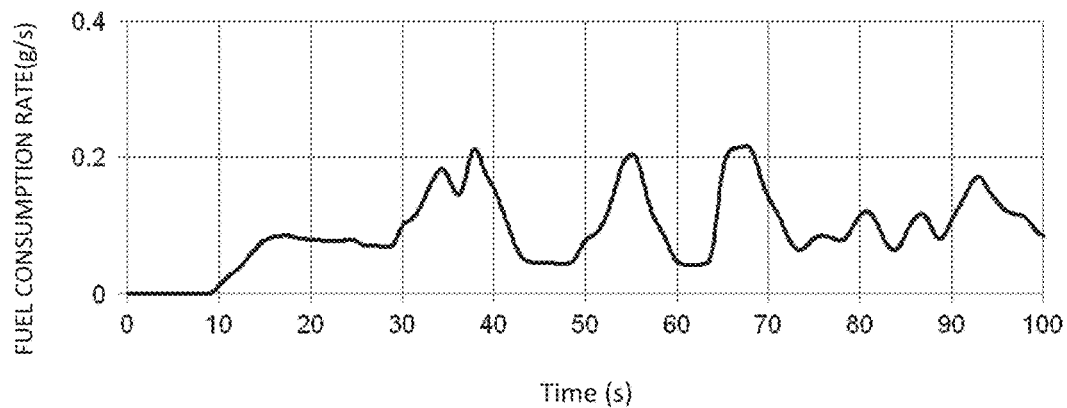
FIG. 5 is a diagram illustrating measurement results of fuel consumption from 0 to 100 seconds by the real-time measurement by the fuel consumption measuring apparatus of the present embodiment and by the real-time measurement by the dilute stream method (in the case of the cold start phase)
Figure 5:
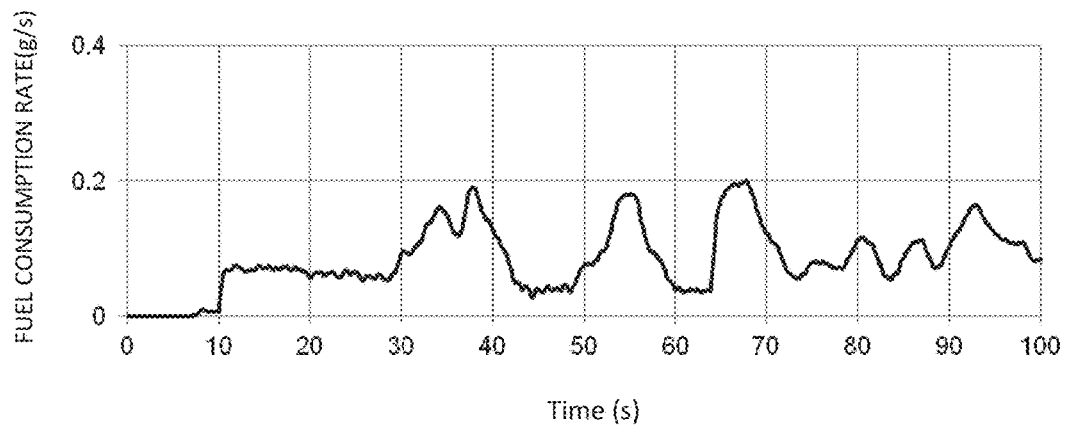

Next, in the cold start phase of the FTP-75 cycle, a result of real-time measurement using the fuel consumption measuring apparatus 100 of the present embodiment, and a result of real-time measurement that obtains an exhaust gas flow rate by a dilute stream method, and uses a value of the exhaust gas flow rate to obtain fuel consumption by a carbon balance method are illustrated in FIGS. 4 and 5. In addition, the dilute stream method refers to a measuring technique that, from the concentration of gas diluted by a CVS and a flow rate after the dilution, obtains exhaust gas weight (flow rate), and from the exhaust gas flow rate obtained by using the dilute stream method, and respective component concentration values obtained by using an exhaust gas analyzer to continuously measure the exhaust gas diluted by the CVS, the fuel consumption is obtained by using the carbon balance method.

FIG. 4(1) illustrates the measurement result using the dilute stream method (conventional method), FIG. 4(2) illustrates the measurement result using the fuel consumption measuring apparatus of the present embodiment, FIG. 4(3) illustrates an AFR obtained by an air-fuel ratio meter, and FIG. 4(4) illustrates vehicle speed. Also, FIG. 5(1) illustrates the measurement result of the fuel consumption from 0 to 100 seconds by the conventional method, and FIG. 5(2) illustrates the measurement result of the fuel consumption from 0 to 100 seconds in the present embodiment.

As can be seen from FIG. 5(1), in the case of the dilute stream method, it turns out that at the time of a small flow rate immediately after the start, a gas delay is noticeable, and a rise in fuel consumption is blunt. On the other hand, as can be seen from FIG. 5(2), in the case of the fuel consumption measuring apparatus of the present embodiment, it turns out that even at the time of a small flow rate immediately after the start, a rise is sharp, and a response delay is reduced. Also, at the time of a fuel cut, the fuel consumption rate is supposed to be almost zero; however, in the case of the dilute stream method, it turns out that a response delay appears (see FIG. 4(1)). On the other hand, in the case of the fuel consumption measuring apparatus of the present embodiment, it turns out that almost simultaneously with a fuel cut, the fuel consumption rate becomes almost zero (see FIG. 4(2)).

Figure 6:
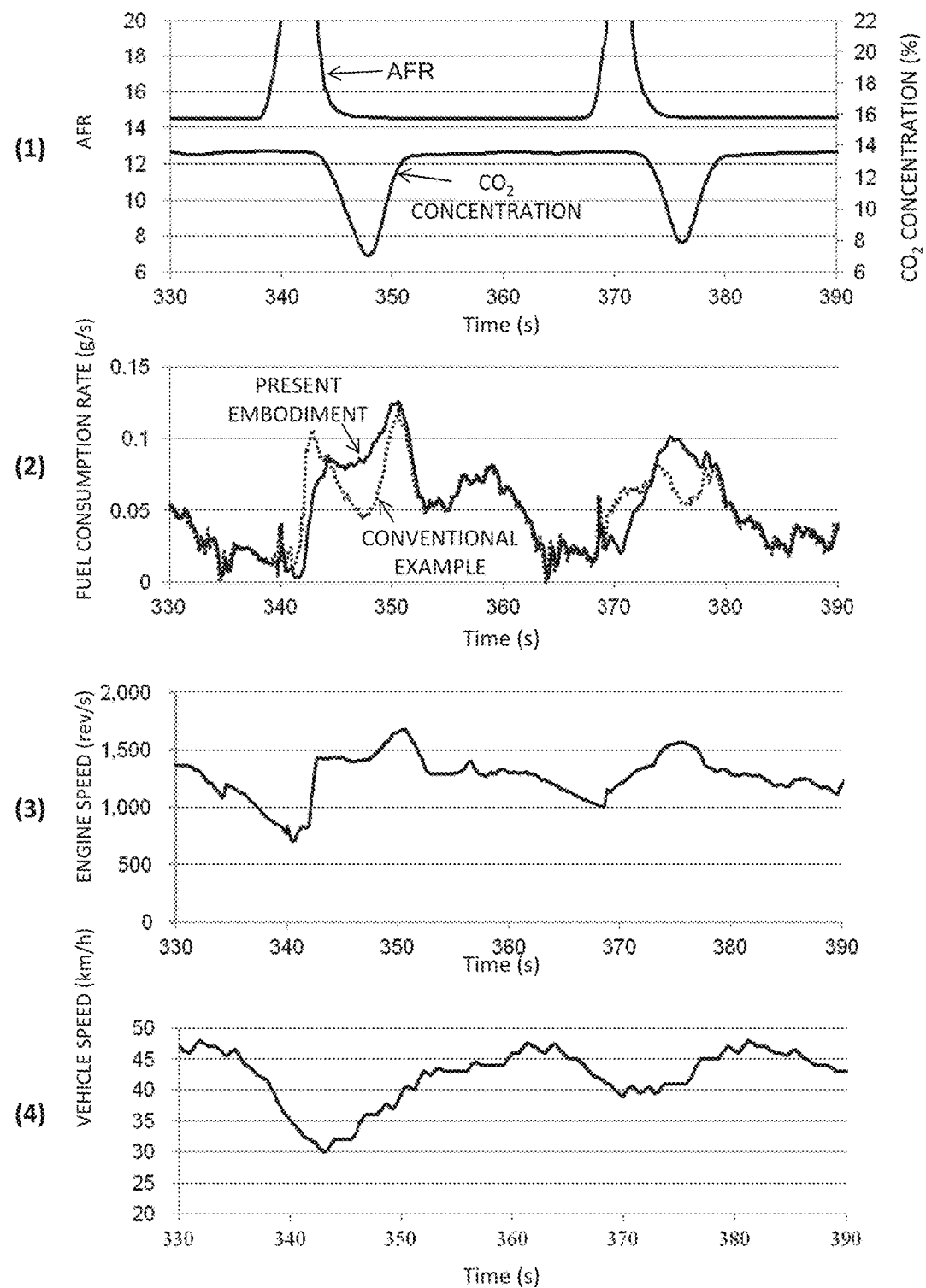
FIG. 6 is a diagram illustrating results of the real-time measurement by the fuel consumption measuring apparatus of the present embodiment and the real-time measurement by the dilute stream method, and the like (in the case of rapid acceleration immediately after a fuel cut in the transient phase)

Next, a result of real-time measurement using the fuel consumption measuring apparatus of the present embodiment and a result of real-time measurement by the dilute stream method (conventional method) in the case of rapid acceleration immediately after a fuel cut in the transient phase of the FTP-75 cycle are illustrated in FIG. 6.

FIG. 6(1) illustrates an AFR obtained by an air-fuel ratio meter, and $CO_2$ concentration that is contained in exhaust gas before dilution by a CVS and obtained by a $CO_2$ meter, FIG. 6(2) illustrates the measurement result using the fuel consumption measuring apparatus of the present embodiment, and the measurement result of obtaining an exhaust gas flow rate by the dilute stream method, and using a value of the exhaust gas flow rate to obtain fuel consumption by the carbon balance method, FIG. 6(3) illustrates engine speed [rpm], and FIG. 6(4) illustrates vehicle speed.

FIG. 6 shows that in the calculation of the fuel consumption by the carbon balance method, the contribution of $CO_2$ weight is very high, and consequently the $CO_2$ concentration exerts a large influence. That is, referring to the AFR in FIG. 6(1), when a fuel cut is performed at the time of deceleration, the AFR rapidly rises to exhibit a lean state. When the engine speed and vehicle speed start to rise, the fuel cut is stopped, and the AFR returns to a stoichiometric (theoretical air-fuel ratio) state. In the case of the dilute stream method, even though the fuel cut is stopped to start acceleration, due to a gas delay, the $CO_2$ concentration remains reduced. For this reason, an influence of the gas response delay appears in the instantaneous fuel consumption, and a difference appears with respect to the fuel consumption measuring apparatus of the present embodiment. Also, in the case of comparing the fuel consumption measuring apparatus of the present embodiment and the dilute stream method with each other, the fuel consumption measuring apparatus of the present embodiment can more accurately measure the instantaneous fuel consumption.

As described, the present embodiment is one that directly and simultaneously measures the flow rate and air-fuel ratio of the exhaust gas flowing through the exhaust gas flow path R by the ultrasonic flow rate sensor 2 and the air-fuel ratio sensor 3; can eliminate a response delay that has been caused by providing a conventional sampling flow path; and also has no need to take into account a difference in delay time or response speed between the respective sensors 2 and 3. This enables the fuel consumption of the engine to be measured at high response speed and with high accuracy. Also, because of using the ultrasonic flow rate sensor 2, pressure loss due to providing the ultrasonic flow rate sensor 2 is not present; measurement accuracy is high over a range from a small flow rate to a large flow rate; and there is also less influence on pulsation. This also enables the fuel consumption to be measured with high accuracy. Further, because of the direct measurement, a piping configuration can be simplified by eliminating the need for the conventional sampling flow path, and also because a dilution device such as a CVS becomes unnecessary, the measuring apparatus can be downsized. In addition, for these reasons, apparatus cost can also be reduced.

Further, on the basis of the air-fuel ratio AFR obtained from the air-fuel ratio sensor 3, the fuel consumption calculation part 41 of the present embodiment changes the exhaust gas density $D_{EX}$ used for the calculation of the fuel consumption Fe, and then calculates the fuel consumption Fe.

Figure 7:
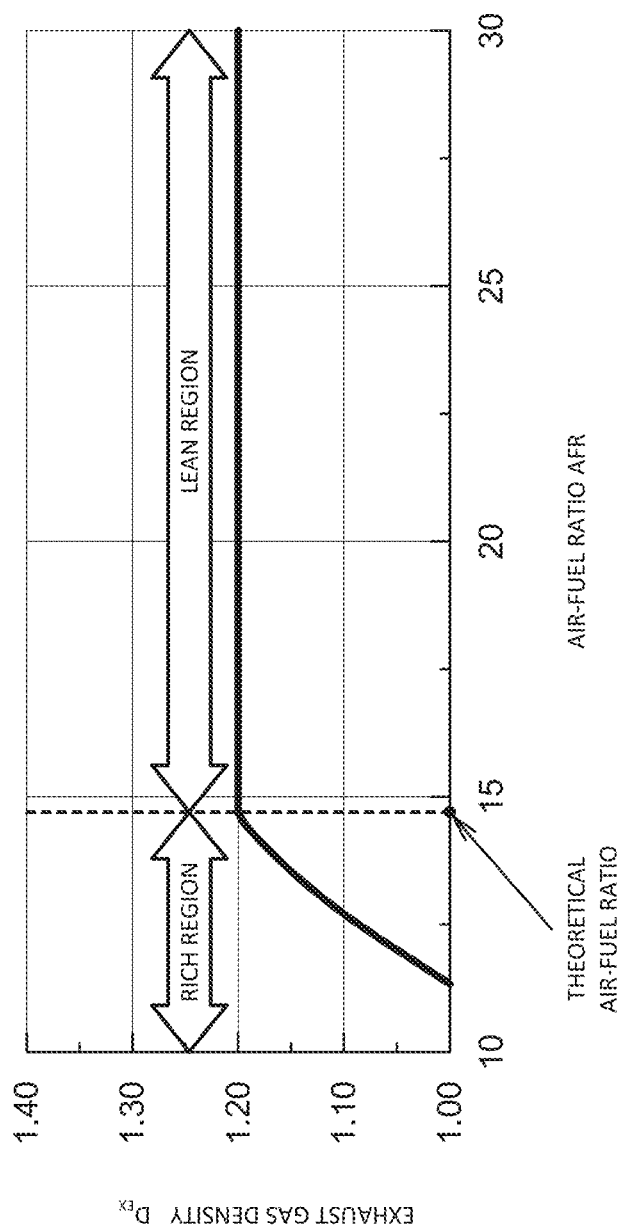
FIG. 7 is a graph illustrating a relationship between an air-fuel ratio and exhaust gas density.

Note that as illustrated in FIG. 7, the exhaust gas density $D_{EX}$ is substantially constant in the region (lean region) where the air-fuel ratio AFR is larger than the theoretical air-fuel ratio (stoichiometry), and in the region (rich region) where the air-fuel ratio AFR is smaller than the theoretical air-fuel ratio, changes along with a change in air-fuel ratio AFR. For this reason, in the case where the air-fuel ratio AFR is included in the rich region, the fuel consumption calculation part 41 changes the exhaust gas density $D_{EX}$ on the basis of the air-fuel ratio AFR, and in the case where the air-fuel ratio AFR is included in the lean region, uses a predetermined constant value as the exhaust gas density $D_{EX}$.

Specifically, the fuel consumption calculation part 41 compares the air-fuel ratio AFR obtained from the air-fuel ratio sensor 3 with the theoretical air-fuel ratio, and in the case where the air-fuel ratio AFR is smaller than the theoretical air-fuel ratio, uses the air-fuel ratio AFR to change the exhaust gas density $D_{EX}$.

The related data storage part 42 of the calculation unit 4 stores related data indicating a relationship between an air-fuel ratio AFR and exhaust gas density $D_{EX}$ in the rich region. As the related data, for example, (1) relational expression data indicating a relational expression between the air-fuel ratio AFR and the exhaust gas density $D_{EX}$ in the rich region, (2) table data indicating a table of each air-fuel ratio AFR and exhaust gas density $D_{EX}$ corresponding to the air-fuel ratio in the rich region, or the like is possible. Such related data is preliminarily stored using unillustrated input means.

Note that the relationship between the air-fuel ratio AFR and the exhaust gas density $D_{EX}$ in the rich region is different depending on the type of fuel, and therefore the related data storage part 42 stores the related data for each fuel type. In the case where the related data storage part 42 stores the related data for each fuel type as described, for example, a user uses the input means to input the type of fuel used for an engine or a vehicle to be subjected to the fuel consumption measurement, and thereby the fuel consumption calculation part 41 uses related data corresponding to the inputted fuel type to change the exhaust gas density $D_{EX}$.

In the calculation unit 4 configured as described, in the case of determining the air-fuel ratio AFR obtained by the air-fuel ratio sensor 3 to be in the rich region, the fuel consumption calculation part 41 uses the relational expression or the table to determines the exhaust gas density $D_{EX}$ (variable) at the air-fuel ratio AFR, and from the exhaust gas density $D_{EX}$ (variable), the exhaust gas flow rate $Q_{EX}$, and the air-fuel ratio AFR, calculates the fuel consumption Fe. On the other hand, in the case of determining the air-fuel ratio AFR obtained by the air-fuel ratio sensor 3 to be in the lean region, the fuel consumption calculation part 41 calculates the fuel consumption Fe from the exhaust gas density $D_{EX}$ (constant) having the predetermined constant value, the exhaust gas flow rate $Q_{EX}$, and the air-fuel ratio AFR.

Effects of First Embodiment

According to the fuel consumption measuring apparatus 100 according to the present embodiment configured as described, the exhaust gas density $D_{EX}$ used for the calculation of the fuel consumption Fe is changed on the basis of the air-fuel ratio AFR obtained by the air-fuel ratio sensor 3, and therefore a measurement error of the fuel consumption Fe of the engine can be reduced. Also, the fuel consumption measuring apparatus 100 is one that directly and simultaneously measures the flow rate $Q_{EX}$ and air-fuel ratio AFR of the exhaust gas flowing through the exhaust gas flow path R by the ultrasonic flow rate sensor 2 and the air-fuel ratio sensor 3; can eliminate a response delay that has been caused by providing a conventional sampling flow path; and also has no need to take into account a difference in delay time or response speed between the respective sensors 2 and 3. For these reasons, the fuel consumption Fe of the engine can be measured at high response speed and with high accuracy.

Further, because of using the ultrasonic flow rate sensor 2, pressure loss due to providing the ultrasonic flow rate sensor 2 is not present; measurement accuracy is high over a range from a small flow rate to a large flow rate; and there is also less influence on pulsation. This also enables the fuel consumption Fe to be measured with high accuracy.

Still further, because of the direct measurement, a piping configuration can be simplified by eliminating the need for the conventional sampling flow path, and also because a dilution device such as a CVS becomes unnecessary, the measuring apparatus can be downsized. In addition, for these reasons, apparatus cost can also be reduced.

Variations of First Embodiment

Note that the present invention is not limited to the first embodiment.

For example, the first embodiment is adapted such that the calculation unit 4 changes the exhaust gas density $D_{EX}$ only in the case where the air-fuel ratio AFR is included in the rich region; however, the present invention may be adapted to, even in the lean region, change the exhaust gas density $D_{EX}$ on the basis of the air-fuel ratio.

Also, the first embodiment is configured to, in the related data storage part, store the related data on an air-fuel ratio and exhaust gas density preliminarily obtained; however, the present invention may be configured such that from the air-fuel ratio obtained by the air-fuel ratio sensor, the fuel consumption calculation part 41 estimates respective component concentrations to calculate the exhaust gas density, and uses the calculated exhaust gas density to calculate the fuel consumption.

Second Embodiment

Next, a second embodiment of the fuel consumption measuring apparatus used for the exhaust gas measuring apparatus according to the present invention is described with reference to drawings.

Figure 8:
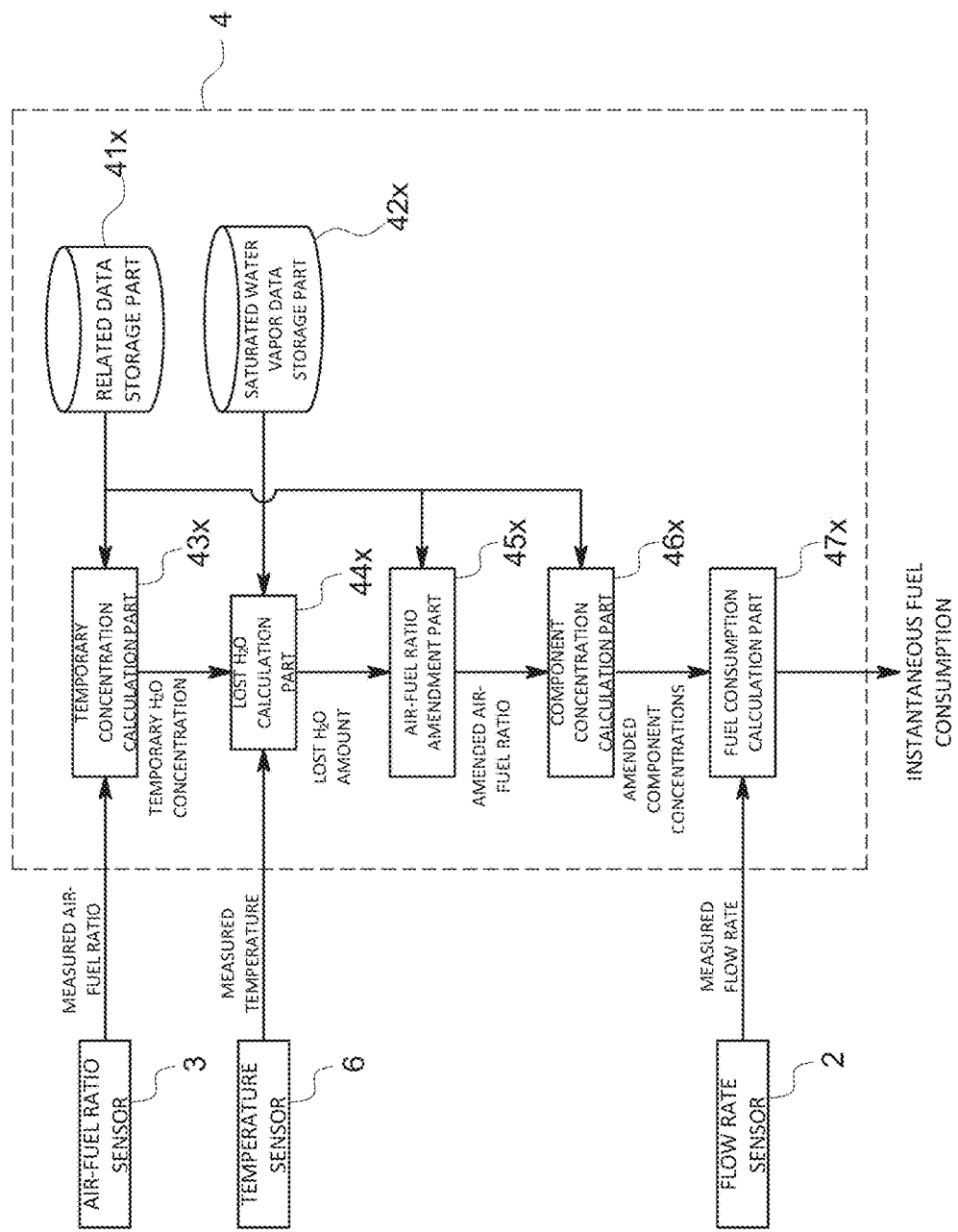
FIG. 8 is a functional block diagram of a fuel consumption calculation unit of the present embodiment.

Also, the fuel consumption calculation unit 4 fulfills functions as a related data storage part 41x, saturated water vapor data storage part 42x, temporary concentration calculation part 43x, lost $H_2O$ calculation part 44x, air-fuel ratio amendment part 45x, component concentration calculation part 46x, fuel consumption calculation part 47x, and the like as illustrated in FIG. 8 by the CPU and its peripheral devices that cooperate according to a predetermined program stored in the memory.

Operation

Next, operation of the fuel consumption measuring apparatus 100 is described together with detailed description of the respective parts of the fuel consumption calculation unit 4.

Figure 10:
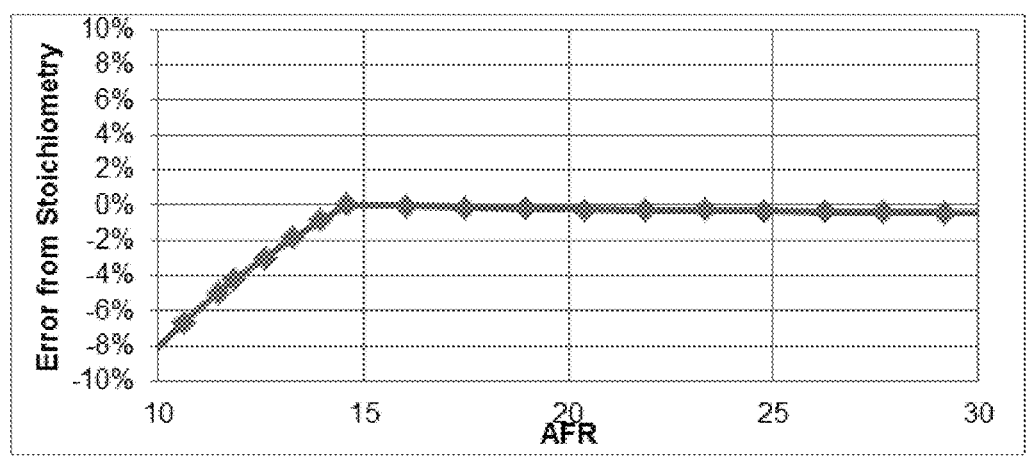
FIG. 10 is a graph illustrating a relationship between an air-fuel ratio and exhaust gas density.

The related data storage part 41x is, for example, as illustrated in FIG. 9, made to store a relationship between concentrations of respective components contained in exhaust gas and an air fuel ratio. In detail, depending on a fuel type (e.g., gasoline), parameters such as a water gas reaction constant (K), a ratio between H and C (H/C), a ratio between O and C (O/C), a molar proportion of $O_2$ to the entire gas ($PO_2$), and molecular weights of C, H, and O are fixed, and therefore on the basis of the parameters, a theoretical air-fuel ratio A/F0 can be calculated to thereby obtain a relationship between an air-fuel ratio and exhaust gas density as illustrated in FIG. 10.

Figure 11:
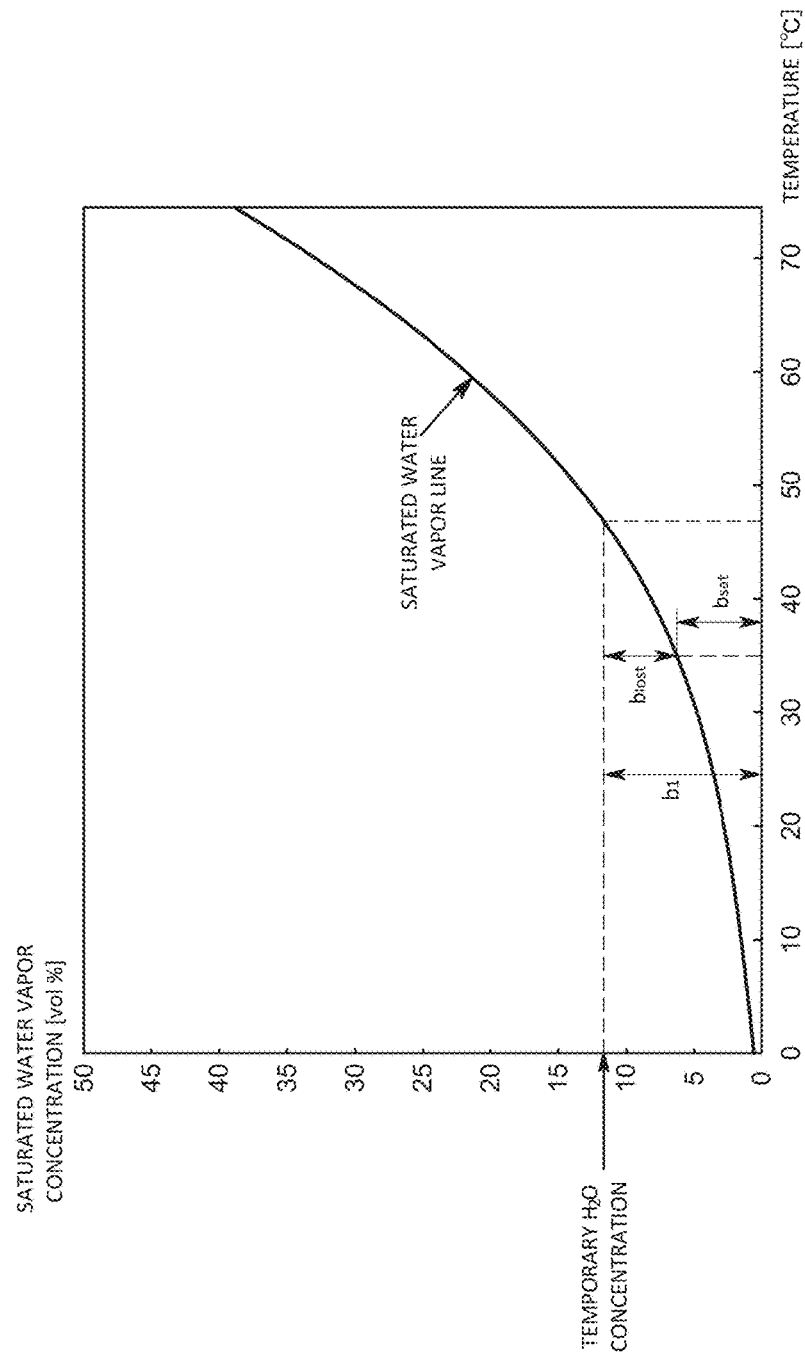
FIG. 11 is a content diagram illustrating contents of a saturated water vapor data storage part in the present embodiment.

Also, the saturated water vapor data storage part 42x is, for example, as illustrated in FIG. 11, made to store a relationship between temperature and saturated water vapor concentration. Such relationships may be shown in the form of a list or as predetermined numerical expressions.

Under such a premise, when an engine is started to emit the exhaust gas, a flow rate, temperature, pressure, and measured air-fuel ratio of the exhaust gas are respectively measured by a flow rate sensor 2, temperature sensor 6, pressure sensor 7, and air-fuel ratio sensor 3.

In doing so, the temporary concentration calculation part 43x refers to the related data storage part 41x to calculate $H_2O$ concentration (hereinafter referred to as temporary $H_2O$ concentration) and concentrations of the other components, i.e., the concentration of $O_2$, concentrations of combustible components, and concentrations of other components (hereinafter referred to as "temporary $O_2$ concentration", and so on) corresponding to the measured air-fuel ratio obtained from the air-fuel ratio sensor 3 (Step 1).

Then, on the basis of a difference between saturated water vapor concentration at the measured temperature obtained from the temperature sensor 6 and the temporary $H_2O$ concentration, the lost $H_2O$ calculation part 44x calculates an amount of $H_2O$ lost by condensation (Step 2).

Subsequently, the air-fuel ratio amendment part 45x takes into account the lost $H_2O$ amount to amend the air-fuel ratio (Step 3).

After that, the component concentration calculation part 46x refers to the related data storage part 41x to calculate respective component concentrations of corresponding to the amended air-fuel ratio obtained as a result of the amendment in Step 3 (Step 4).

Finally, the fuel consumption rate calculation part 47x obtains exhaust gas density from the respective component concentrations obtained in Step 4, and calculates a fuel consumption rate with the exhaust gas density, the amended air-fuel ratio, and the exhaust gas flow rate obtained by the flow rate sensor 2 as at least parameters (Step 5).

Each of the above-described steps is more specifically described.

In Step 1, the temporary concentration calculation part 43x refers to the related data storage part 41x illustrated in FIG. 9 to calculate the $H_2O$ concentration (temporary $H_2O$ concentration) corresponding to the measured air-fuel ratio. The temporary $H_2O$ concentration is considered to approximate to the concentration of $H_2O$ contained in the exhaust gas immediately after the emission from the engine.

Also, at this time, the temporary concentration calculation part 43x also refers to the related data storage part 41x to thereby simultaneously calculate the concentrations of the other components constituting the exhaust gas, i.e., $O_2$, the combustible components (CO, $H_2$, and HC), other components (such as $N_2$). In the following, they are respectively referred to as the temporary $O_2$ concentration, temporary combustible component concentrations, and temporary other component concentrations.

In Step 2, the lost $H_2O$ calculation part 44x refers to the saturated water vapor data storage part 42x illustrated in FIG. 11 to obtain the saturated water vapor concentration at the measured temperature obtained by the temperature sensor 6.

In the case where the saturated water vapor concentration is lower than the temporary $H_2O$ concentration, the lost $H_2O$ calculation part 44x subtracts the saturated water vapor concentration from the temporary $H_2O$ concentration as expressed in the following expression (Expression 4), and calculates a resultant value as the concentration of the lost $H_2O$ lost by condensation and the like. Note that concentration herein refers to volumetric concentration of a predetermined component; however, the concentration can also be expressed as the volume, mole, mass, or the like of the component in 1 m3 of exhaust gas, and therefore they may be treated as equivalents, obviously.

$$b_{lost}=b_1-b_{sat} \qquad \text{[Expression 4]}$$

Here, $b_{lost}$ is the concentration [$m^3/m^3$] of the lost $H_2O$ (or the volume [$m^3$] of the lost $H_2O$ in 1 $m^3$ of the exhaust gas, and the same applies in the following), $b_1$ the temporary $H_2O$ concentration [$m^3/m^3$], and $b_{sat}$ the saturated water vapor concentration [$m^3/m^3$].

The case where the saturated water vapor concentration is lower than the temporary $H_2O$ concentration corresponds to the case where the exhaust gas temperature has a constant value or less on occasions such as a cold start, and in this case, some proportion of $H_2O$ contained in the exhaust gas immediately after the emission from the engine is condensed in a vehicle exhaust pipe to a measuring point by the air-fuel ratio sensor 3, and thereby lost. On the other hand, at the measuring point, $H_2O$ in the exhaust gas is considered to be in a saturated state, and therefore as expressed by the above expression, the value obtained by subtracting the saturated water vapor concentration from the temporary $H_2O$ concentration can be determined as the concentration of the lost $H_2O$.

For example, as illustrated in FIG. 11, in the case where the temporary $H_2O$ concentration $b_1$ is approximately 0.12 (12 vol %) and the measured temperature is 35° C., the lost $H_2O$ concentration $b_{lost}$ has a value indicated by a line with two arrowheads.

Meanwhile, the measured air-fuel ratio is one that is calculated on the basis of the exhaust gas after $H_2O$ has been partially lost by condensation and the like on the way. Accordingly, the exhaust gas to be subjected to the measurement of the measured air-fuel ratio has lower $H_2O$ concentration than a true value, and in other words, the other component concentrations such as the $O_2$ concentration are higher than corresponding true values.

Therefore, in Step 3, on the basis of the value of the lost $H_2O$ concentration, the air-fuel ratio amendment part 45x uses the following manner to amend the temporary concentration of one of the predetermined components other than $H_2O$ obtained in Step 1.

Given that $a_1$ is the temporary $O_2$ concentration [$m^3/m^3$], $b_1$ is the temporary $H_2O$ concentration [$m^3/m^3$], $c_1$ is temporary total combustible component concentration [$m^3/m^3$], and $d_1$ is temporary total other component concentration [$m^3/m^3$], the following expression (Expression 5) holds.

$$a_1+b_1+c_1+d_1=1 \qquad \text{[Expression 5]}$$

Accordingly, by taking into account the volume (amount) of the condensed $H_2O$, a volumetric ratio among the respective components contained in the exhaust gas immediately after the emission from the engine can be expressed by the following expression (Expression 6).

$O_2$ concentration:$H_2O$ concentration:total combustible component concentration:total other component concentration [Expression 6]

$$=a_1:(b_1+b_{lost}):c_1:d_1 \qquad (5)$$

On the basis of the ratio, the air-fuel ratio amendment part 45x calculates concentration of $O_2$ (hereinafter referred to as amended $O_2$ concentration) contained in the exhaust gas immediately after the emission from the engine in a lean condition, or in a rich condition, calculates total concentration of the combustible components (hereinafter referred to as amended total combustible component concentration) contained in the exhaust gas immediately after the emission from the engine.

That is, in the lean condition, the air-fuel ratio amendment part 45x performs an operation equivalent to an expression (Expression 7) below, or in the rich condition, performs an operation equivalent to an expression (Expression 8) below to obtain the amended $O_2$ concentration or the amended total combustible component concentration. Note that the combustible components mainly include $H_2$, CO, and HC, and in practice, concentrations of the components are respectively calculated; however, to facilitate understanding, this specification describes the combustible components as one component. The same holds true for other components ($N_2$ and $CO_2$).

$$a_{amd} = \frac{a_1}{a_1 + b_1 + b_{lost} + c_1 + d_1} = \frac{a_1}{1 + b_{lost}} \quad \text{[Expression 7]}$$

$$c_{amd} = \frac{c_1}{a_1 + b_1 + b_{lost} + c_1 + d_1} = \frac{c_1}{1 + b_{lost}} \quad \text{[Expression 8]}$$

Here, $a_{amd}$ is the amended $O_2$ concentration [m³/m³], and $c_{amd}$ is the amended combustible component concentration [m³/m³].

Subsequently, the air-fuel ratio amendment part 45x refers to the related data storage part 41x to thereby calculate an air-fuel ratio corresponding to the amended $O_2$ concentration in the lean condition, or in the rich condition, corresponding to the amended total combustible component concentration. The air-fuel ratio is the amended air-fuel ratio, and considered to have a value closer to a true value.

In Step 4, the component concentration calculation part 46x refers to the related data storage part 41x, and makes an amendment to calculate the respective component concentrations corresponding to the amended air-fuel ratio. For example, in the lean condition, the amended $O_2$ concentration has been already obtained in Step 3, and therefore the concentrations of the other components, i.e., the total combustible component concentration, $H_2O$ concentration, and total other component concentration are calculated. Also, in the rich condition, the amended total combustible component concentration has been already obtained in Step 3, and therefore the concentrations of the other components, i.e., the $O_2$ concentration, $H_2O$ concentration, and total other component concentration are calculated. In addition, in the following, the respective component concentrations obtained in the component concentration calculation part 46x are referred to as amended $H_2O$ concentration, and so on.

In Step 5, the fuel consumption rate calculation part 47x obtains the exhaust gas density $D_{EX}$ from the amended concentrations of the respective components, which have been subjected to the amendment and calculation in the component concentration calculation part 46x. Specifically, the fuel consumption rate calculation part 47x performs an operation equivalent to the following expression (Expression 9).

$$D_{EX} = a_{amd} \times D_{O2} + b_{amd} \times D_{H2O} + c_{amd} \times D_{FLM} + d_{amd} \times D_{ELS} \quad \text{[Expression 9]}$$

Here, $a_{amd}$ is the amended $O_2$ concentration, $DO_2$ is the $O_2$ gas density, $b_{amd}$ is the amended $H_2O$ concentration, $D_{H2O}$ is the $H_2O$ gas density, $d_{amd}$ is the amended total combustible component concentration, $D_{ELS}$ is the total combustible component gas density, $d_{amd}$ is the amended total other component concentration, and $D_{ELS}$ is the total other component gas density. Note that, as described above, to facilitate understanding, the combustible component gases and other component gases are respectively described with pluralities of component gases are respectively lumped together, and in practice, the exhaust gas density is calculated from the concentrations of the respective component gases, and densities of the respective component gases. Note that in this embodiment, the exhaust gas density is obtained from the amended concentrations of the respective component gases; however, without limitation to this, the exhaust gas density may be obtained from the amended air-fuel ratio.

Subsequently, the fuel consumption rate calculation part 47x performs an operation equivalent to the following expression (Expression 10) using the exhaust gas density $D_{EX}$, amended air-fuel ratio AFR, and exhaust gas flow rate $Q_{EX}$ obtained as described above as at least parameters to calculate the instantaneous fuel consumption rate F(t) at time t.

$$Fe(t) = \frac{Q_{EX}(t)}{60} \times D_{EX} \times \frac{1}{AFR(t) + 1} \quad \text{[Expression 10]}$$

Here, Fe(t) is the fuel consumption rate [g/s] at time t, $Q_{EX}$(t) is the exhaust gas flow rate [1/min] at time t in a standard state (temperature: 293.15 k, pressure: 101.3 kPa), AFR(t) is the air-fuel ratio at time t, and $D_{EX}$ is the exhaust gas density [kg/m³].

Effects of Second Embodiment

According to the present embodiment configured as described, the amount of $H_2O$ that is lost in a path to the measuring point for measuring $H_2O$ in the exhaust gas on occasions such as the cold start when the engine and the exhaust gas are not sufficiently warmed is calculated, and by taking into account the lost $H_2O$ amount, the respective component concentrations and air-fuel ratio of the exhaust gas immediately after the emission from the engine are estimated and calculated, so that measurement accuracies of the air-fuel ratio and respective component concentrations are significantly improved as compared with a conventional case. This can also contribute to improvement of measurement accuracies of the fuel consumption and the like obtained from the estimated and calculated results.

Meanwhile, an air-fuel ratio sensor (not illustrated) is provided near an exhaust gas outlet port of the engine, and the use of a value of the air-fuel ratio sensor enables an influence of the lost $H_2O$ to be eliminated, so that in terms of only the air-fuel ratio, higher accurate measurement becomes possible.

However, in doing so, a time lag occurs between the exhaust gas flow rate value obtained as a result of using the ultrasonic flow rate sensor 2 to measure the exhaust gas emitted from a tail pipe and the value of the air-fuel ratio measured using the air-fuel ratio sensor inside a vehicle, and thereby measurement accuracy of the instantaneous fuel consumption is deteriorated.

On the other hand, in the present embodiment, the air-fuel ratio sensor 3 is provided near the ultrasonic flow rate sensor 2, and therefore a measurement error due to the time lag can be reduced to obtain accurate instantaneous fuel consumption.

Further, because of using the ultrasonic flow rate sensor 2, pressure loss due to providing the ultrasonic flow rate sensor 2 is not present; measurement accuracy is high over a range from a small flow rate to a large flow rate; and there is also less influence on pulsation. This also enables the fuel consumption Fe to be measured with high accuracy.

Still further, because of direct measurement, a piping configuration can be simplified, and also because a dilution device such as a CVS becomes unnecessary, the measuring apparatus can be downsized. In addition, for these reasons, apparatus cost can also be reduced.

Variations of Second Embodiment

Note that the present invention is not limited to the second embodiment.

For example, the present invention may be configured to repeat a procedure for setting the amended $H_2O$ concentration calculated in Step 4 as the temporary $H_2O$ concentration, returning to Step 2, and in Step 4 through Step 3, obtaining amended $H_2O$ concentration again, and in the case where a value of the amended $H_2O$ concentration converges within a certain range, proceed to Step 5.

Also, for example, in the case where only the respective component concentrations are necessary, but the air-fuel ratio is not necessary, the present invention may be adapted to, without providing the air-fuel ratio amendment part, in the component concentration calculation part, take into account the lost $H_2O$ amount to amend one temporary component concentration ($O_2$ concentration or total combustible component concentration in this embodiment) of the respective component concentrations, and refer to the related data storage part to calculate the other component concentrations corresponding to the amended one component concentration.

In the embodiment, the temperature sensor doubles as one used for the ultrasonic flow rate sensor, but may be separately provided as a dedicated one. In such a case, it is desirable to attach the dedicated temperature sensor to a position as close to the tail pipe as possible. Further, the present invention can also be adapted to obtain a value of the temperature sensor inside the vehicle, and use the value to obtain the saturated water vapor concentration.

Other Embodiments

The flow rate sensor 2 in each of the above-described embodiments is the ultrasonic flow rate sensor; however, besides, various types of flow rate sensors such as a differential pressure type flow rate sensor, thermal type flow rate sensor, and Coriolis type flow rate sensor can be used. The air-fuel ratio sensor is also not limited to the zirconia type one.

Further, in each of the above-described embodiments, the air-fuel ratio sensor 3 is provided on the downstream side of the flow rate sensor 2; however, the air-fuel ratio sensor 3 may be provided on the upstream side of the flow rate sensor 2. Still further, the present invention may be adapted such that the calculation unit 4 receives a signal from the air-fuel ratio sensor provided near the engine exhaust outlet port of the vehicle to calculate the fuel consumption Fe.

In addition, in each of the above-described embodiments, the air-fuel ratio sensor is provided at the exhaust gas lead-out port of the housing, which is on the downstream side of the ultrasonic flow rate sensor; however the air-fuel ratio sensor may be provided on the upstream side of the ultrasonic flow rate sensor, such as at the exhaust gas introduction port of the housing. Also, the present invention may be adapted such that the calculation unit 4 receives the signal from the air-fuel ratio sensor provided near the engine exhaust outlet port of the vehicle to calculate the fuel consumption.

Further, in each of the above-described embodiments, the calculation unit 4 is provided inside the housing 5; however, the calculation unit 4 may be provided outside the housing 5. In such a case, it is possible to, inside the housing 5, provide a wired or wireless transceiver device that transceives data with the calculation unit 4 provided outside. For example, the transceiver device transmits a detection signal of the ultrasonic flow rate sensor and a detection signal of the air-fuel ratio sensor to the calculation unit 5.

In addition, the fuel consumption measuring apparatus of each of the above-described embodiments is unitized in the housing; however, the fuel consumption measuring apparatus may be one that is not unitized.

Figure 12:
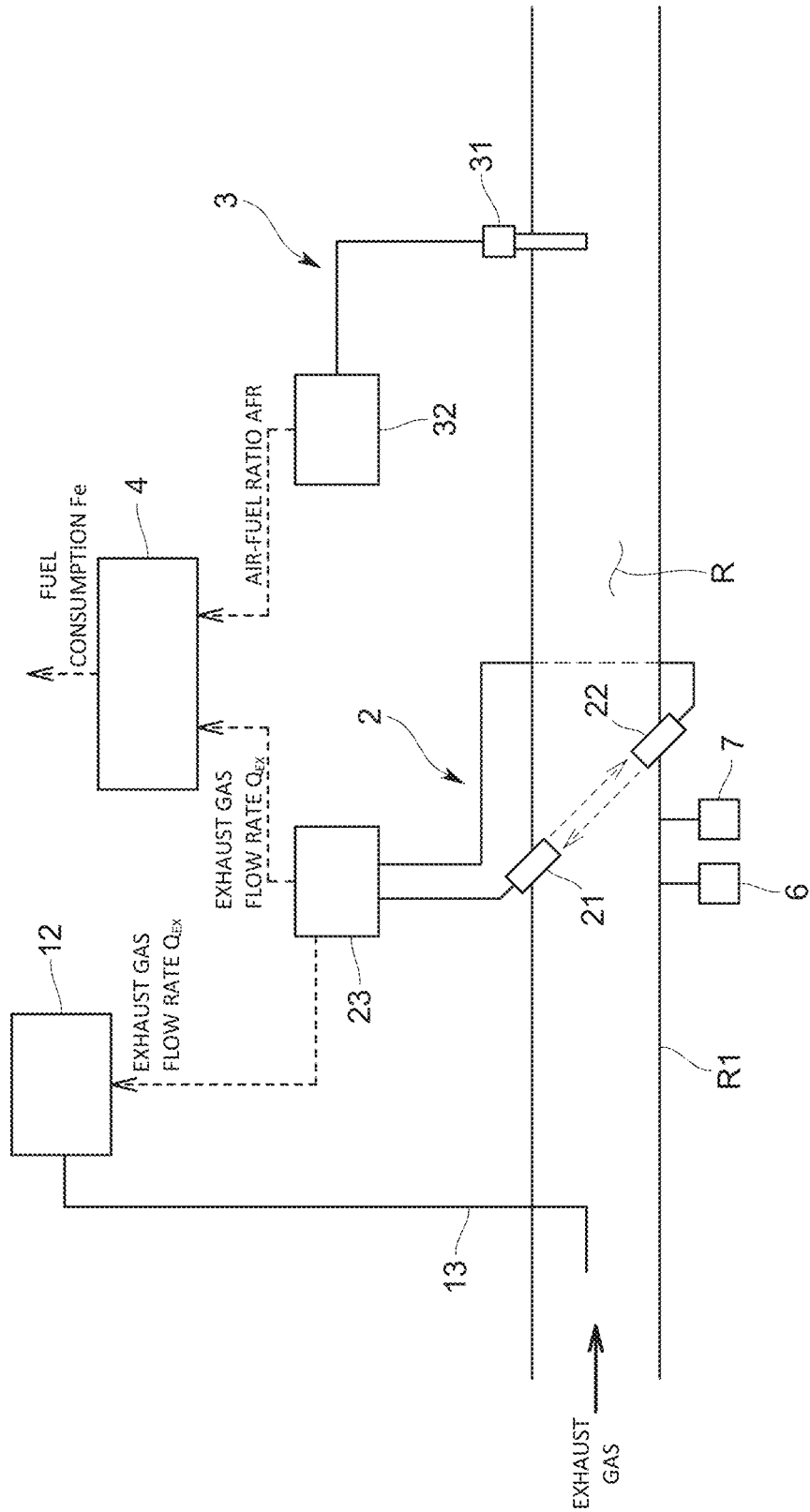
FIG. 12 is a diagram schematically illustrating a configuration of a fuel consumption measuring apparatus of a variation.

Further, the fuel consumption measuring apparatus 100 may be, as illustrated in FIG. 12, provided with an exhaust gas analyzer 12 that analyzes a predetermined measurement target component contained in the exhaust gas flowing through the exhaust gas flow path R. In addition, a calculation part of the exhaust gas analyzer 12 uses obtained component concentration and the exhaust gas flow rate obtained by the ultrasonic flow rate sensor to calculate emission mass of the measurement target component. In doing so, the ultrasonic flow rate sensor 3 can be used for both of the fuel consumption measurement and the emission mass measurement (mass measurement). Note that not the calculation part of the exhaust gas analyzer 12, but the calculation unit 4 of the fuel consumption measuring apparatus 100 may use the component concentration obtained by the exhaust gas analyzer 12 and the exhaust gas flow rate obtained by the ultrasonic flow rate sensor 3 to calculate the emission mass of the measurement target component.

Desirably, the exhaust gas analyzer 12 measures the measurement target component contained in the exhaust gas flowing on the upstream side of the ultrasonic flow rate sensor 3 in the exhaust gas flow path R. Specifically, a sampling pip 13 for sampling part of the exhaust gas flowing through the exhaust gas flow path R to introduce the part into the exhaust gas analyzer 12 is connected on the upstream side of the ultrasonic flow rate sensor 3. Note that in the case of the configuration where the sampling pipe 13 is used to sample the exhaust gas, desirably, the calculation unit 4 uses a sampling flow rate of the sampled exhaust gas flowing through the sampling pipe 13 to amend the exhaust gas flow rate obtained by the ultrasonic flow rate sensor 3.

Besides, it should be appreciated that the present invention is not limited to any of the above-described embodiments, but can be variously modified without departing from the scope thereof.

REFERENCE SIGNS LIST

100: Fuel consumption measuring apparatus
E: Engine
R: Exhaust gas flow path
2: Flow rate sensor
3: Air-fuel ratio sensor
4: Calculation unit
41: Fuel consumption calculation part
42: Related data storage part

What is claimed is:
1. A fuel consumption measuring apparatus that measures fuel consumption of an engine, the fuel consumption measuring apparatus comprising:

an exhaust gas flow path that is connected to a tail pipe of an exhaust pipe of the engine such that exhaust gas emitted from the tail pipe is introduced;

a flow rate sensor that is provided in the exhaust gas flow path and measures a flow rate of the exhaust gas flowing through the exhaust gas flow path;

an air-fuel ratio sensor that is provided downstream the tail pipe and a catalyst associated with the engine in the exhaust gas flow path and measures an air-fuel ratio;

a related data storage part that stores related data indicating a relationship between an air-fuel ratio and exhaust gas density; and a calculation unit that changes exhaust gas density on a basis of the air-fuel ratio and the related data, and that calculates the fuel consumption of the engine with use of the flow rate of the exhaust gas, the air-fuel ratio, and the changed exhaust gas density.

2. The fuel consumption measuring apparatus according to claim 1, wherein the calculation unit, in a case where the air-fuel ratio is included in a rich region, changes the exhaust gas density, and in a case where the air-fuel ratio is included in a lean region, uses a predetermined constant value as the exhaust gas density.

3. The exhaust gas measuring apparatus according to claim 1, further comprising:

a flow conditioner that is provided on the upstream side of the flow rate sensor in the exhaust gas flow path.

4. An exhaust gas measuring apparatus comprising:

an air-fuel ratio sensor provided in an exhaust gas flow path that is connected to a tail pipe of an exhaust pipe of an engine such that the air-fuel ratio sensor is downstream the tail pipe and a catalyst associated with the engine;

a temperature sensor that measures temperature of the exhaust gas emitted from the tail pipe;

a related data storage part that stores related data that defines a relationship between concentration of each component contained in the exhaust gas and an air-fuel ratio;

a temporary concentration calculation part that refers to the related data storage part to calculate temporary $H_2O$ concentration that is $H_2O$ concentration corresponding to a measured air-fuel ratio obtained from the air-fuel ratio sensor; and a lost $H_2O$ calculation part that, on a basis of saturated water vapor concentration at the exhaust gas temperature measured by the temperature sensor and the temporary $H_2O$ concentration, calculates a lost $H_2O$ amount that is an amount of $H_2O$ lost by condensation and the like in a path to a measuring point of the air-fuel ratio sensor to improve measurement accuracy of the air-fuel ratio sensor.

5. The exhaust gas measuring apparatus according to claim 4, further comprising an air-fuel ratio amendment part that takes into account the lost $H_2O$ amount to amend the measured air-fuel ratio.

6. The exhaust gas measuring apparatus according to claim 5, further comprising a component concentration calculation part that refers to the related data storage part to calculate each component concentration corresponding to an amended air-fuel ratio that is the measured air-fuel ratio amended in the air-fuel ratio amendment part.

7. The exhaust gas measuring apparatus according to claim 6, further comprising:

a density calculation part that calculates exhaust gas density on a basis of the each component concentration calculated in the component concentration calculation part; and a fuel consumption calculation part that calculates fuel consumption of the engine on a basis of the exhaust gas density and the amended air-fuel ratio.

8. The exhaust gas measuring apparatus according to claim 4, wherein the temporary concentration calculation part refers to the related data storage part to calculate respective component concentrations corresponding to the measured air-fuel ratio obtained from the air-fuel ratio sensor, the exhaust gas measuring apparatus further comprising a component concentration calculation part that takes into account the lost $H_2O$ amount to amend one component concentration of the respective component concentrations calculated by the temporary concentration calculation part, and refers to the related data storage part to calculate the other component concentrations corresponding to the amended one component concentration.

9. The exhaust gas measuring apparatus according to claim 4, wherein the related data storage part stores the related data for each fuel type.

10. A fuel consumption measuring method for measuring fuel consumption of an engine with use of an exhaust gas flow rate, an air-fuel ratio and exhaust gas density, the fuel consumption measuring method comprising:

changing the exhaust gas density on a basis of the air-fuel ratio obtained by an air-fuel ratio sensor and related data indicating a relationship between an air-fuel ratio and exhaust gas density, wherein the air-fuel ratio sensor being is provided in an exhaust gas flow path that is connected to a tail pipe of an exhaust pipe of the engine such that the air-fuel ratio sensor is downstream the tail pipe and a catalyst associated with the engine, and measures a ratio of air to fuel of exhaust gas flowing through the exhaust gas flow path; and calculating the fuel consumption, with use of the exhaust gas flow rate obtained by a flow rate sensor that is provided and measures a flow rate of the exhaust gas flowing through the exhaust gas flow path the air-fuel ratio obtained by the air-fuel ratio sensor and the changed exhaust gas density.

\* \* \* \* \*